United States Patent
Glazier et al.

(10) Patent No.: US 8,355,136 B2
(45) Date of Patent: Jan. 15, 2013

(54) SUB-MICRON SURFACE PLASMON RESONANCE SENSOR SYSTEMS

(75) Inventors: James A. Glazier, Bloomington, IN (US); Dragos Amarie, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 46 days.

(21) Appl. No.: 13/158,502

(22) Filed: Jun. 13, 2011

(65) Prior Publication Data

US 2011/0257494 A1 Oct. 20, 2011

Related U.S. Application Data

(60) Continuation-in-part of application No. 12/751,099, filed on Mar. 31, 2010, now Pat. No. 7,961,329, and a continuation-in-part of application No. 12/751,101, filed on Mar. 31, 2010, now Pat. No. 7,961,330, which is a division of application No. 11/611,509, filed on Dec. 15, 2006, now Pat. No. 7,724,373, said application No. 12/751,099 is a division of application No. 11/611,509.

(60) Provisional application No. 60/750,872, filed on Dec. 16, 2005.

(51) Int. Cl.
*G01N 21/55* (2006.01)
*A61B 5/145* (2006.01)
(52) U.S. Cl. ......... 356/445; 356/436; 600/310; 600/318
(58) Field of Classification Search .......... 356/445–448, 356/432–440; 600/310, 318, 315, 584; 435/6, 435/7, 9, 40.5, 287.2
See application file for complete search history.

(56) References Cited

U.S. PATENT DOCUMENTS

| | | | |
|---|---|---|---|
| 5,395,587 A | 3/1995 | Brigham-Burke et al. |
| 5,606,633 A | 2/1997 | Groger et al. |
| 5,858,195 A | 1/1999 | Ramsey |
| 5,986,808 A | 11/1999 | Wang |
| 6,208,883 B1 | 3/2001 | Holupka et al. |
| 6,375,871 B1 | 4/2002 | Bentsen et al. |
| 6,480,282 B1 | 11/2002 | Chinowsky et al. |
| 6,579,721 B1 | 6/2003 | Natan et al. |
| 6,592,519 B1 | 7/2003 | Martinez |
| 6,660,381 B2 | 12/2003 | Halas et al. |
| 6,801,317 B2 | 10/2004 | Hofmann |
| 6,835,534 B2 | 12/2004 | Weiss et al. |
| 6,947,145 B2 | 9/2005 | Naya |
| 6,956,651 B2 | 10/2005 | Lackritz et al. |
| 7,074,621 B2 | 7/2006 | Latov et al. |
| 7,118,710 B2 | 10/2006 | Cunningham |
| 7,129,096 B2 | 10/2006 | Chilkoti et al. |
| 7,142,296 B2 | 11/2006 | Cunningham et al. |

(Continued)

OTHER PUBLICATIONS

Rice, Todd W., et al, "Therapeutic Intervention and Targets for Sepsis", Annu. Rev. Med., 2005, vol. 56, pp. 225-248.

(Continued)

*Primary Examiner* — Hoa Pham
(74) *Attorney, Agent, or Firm* — Barnes & Thornburg LLP

(57) ABSTRACT

Wearable or implantable devices combining microfluidic control of sample and reagent flow and micro-cavity surface plasmon resonance sensors functionalized with surface treatments or coatings capable of specifically binding to target analytes, ligands, or molecules in a bodily fluid are provided. The devices can be used to determine the presence and concentration of target analytes in the bodily fluids and thereby help diagnose, monitor or detect changes in disease conditions.

39 Claims, 20 Drawing Sheets

U.S. PATENT DOCUMENTS

| | | | |
|---|---|---|---|
| 7,724,373 B2 * | 5/2010 | Glazier et al. | 356/445 |
| 7,961,329 B2 * | 6/2011 | Glazier et al. | 356/445 |
| 7,961,330 B2 * | 6/2011 | Glazier et al. | 356/445 |
| 8,169,615 B2 * | 5/2012 | Glazier et al. | 356/445 |
| 2002/0031838 A1 | 3/2002 | Meinhart et al. | |
| 2002/0187074 A1 | 12/2002 | O'Connor et al. | |
| 2003/0059820 A1 | 3/2003 | Vo-Dinh | |
| 2003/0231304 A1 | 12/2003 | Chan et al. | |
| 2004/0005582 A1 | 1/2004 | Shipwash | |
| 2004/0012788 A1 * | 1/2004 | Nakajima et al. | 356/445 |
| 2004/0238484 A1 | 12/2004 | Le Pioufle et al. | |
| 2006/0134704 A1 | 6/2006 | Muraguchi et al. | |
| 2006/0246510 A1 | 11/2006 | Densham | |
| 2008/0088845 A1 | 4/2008 | Ke et al. | |
| 2008/0264151 A1 | 10/2008 | Sullivan et al. | |
| 2009/0073447 A1 | 3/2009 | Dahint et al. | |
| 2009/0302235 A1 | 12/2009 | Himmelhaus | |
| 2011/0060198 A1 * | 3/2011 | Bennett et al. | 600/310 |

OTHER PUBLICATIONS

Karlsson, Robert, et al., "Surface Plasmon Resonance Detection and Multispot Sensing for Direct Monitoring of Interactions Involving Low-Molecular-Weight Analytes and for Determination of Low Affinities", Analytical Biochemistry, 1995, vol. 228, pp. 274-280.

Endo, Tatsuro, et al., "Label-Free Detection of Peptide Nucleic Acid-DNA Hybridization Using Localized Surface Plasmon Resonance Based Optical Biosensor", Analytical Chemistry, Nov. 1, 2005, vol. 77, No. 21, pp. 6976-6984.

Technology, New Scientist, Nov. 5, 2005, www/.newscientist.com, pp. 1.

Endo, Tatsuro, et al., "Multiple Label-Free Detection of Antigen-Antibody Reaction Using Localized Surface Plasmon Resonance-Based Core-Shell Structured Nanoparticle Layer Nanochip", Anal. Chem., Sep. 15, 2006, vol. 78, No. 18, pp. 6465-6475.

Hutter, Eliza, et al., "Exploitation of Localized Surface Plasmon Resonance", Adv., Matr, Oct. 4, 2004, vol. 16, No. 19, pp. 1685-1706.

* cited by examiner

SUB-MICRON SURFACE PLASMON RESONANCE SENSOR SYSTEMS

CROSS-REFERENCE TO RELATED APPLICATIONS

This application is a continuation-in-part application of U.S. patent application Ser. No. 12/751,099, filed Mar. 31, 2010, entitled "Sub-Micron Surface Plasmon Resonance Sensor Systems" and U.S. patent application Ser. No. 12/751, 101, filed Mar. 31, 2010, entitled "Sub-Micron Surface Plasmon Resonance Sensor Systems," which are divisional applications of U.S. patent application Ser. No. 11/611,509, filed Dec. 15, 2006, entitled "Sub-Micron Surface Plasmon Resonance Sensor Systems," which claims priority under 35 U.S.C. §119(e) to U.S. provisional application Ser. No. 60/750,872, filed on Dec. 16, 2005, entitled "Sub-micron Cavity Surface Plasmon Sensors and Their Micro-fluidic Applications", the entire disclosure of each is incorporated by reference herein.

GOVERNMENTAL INTEREST

This invention was made with government support under IBN-0083653 and NAG2-1619 awarded by the National Science Foundation and from NASA. The U.S. Government has certain rights in the invention.

BACKGROUND

A significant advance in contemporary medicine is the introduction of point of care (POC) devices (POCd) for rapid, portable diagnosis. POCd provide rapid turnaround which aids therapeutic decisions, quick dissemination of test results to patients, thereby reducing physician workload and increasing patient satisfaction, reduced paper work, simplified sample tracking, and reduced need for specialized technicians. Despite numerous technological advances in the field of biosensors and biomarkers, currently, POCd's performance is limited to blood tests for glucose and cholesterol levels, blood pressure monitors, pregnancy tests, urine dipstick tests, scales, thermometers, otoscopes, and ophthalmoscopes only. Among them the blood glucose monitor occupies the largest POCd diagnostic sector and is the only one vastly available and affordable, followed by the cardiac and congestive heart failure POCd which are far behind, but the next fastest growing segment. POCd tests administered as multiplex panels provide further significant benefits by allowing screening of several cardiac markers in parallel with several other infectious markers and drugs of abuse, simultaneously saving time and providing comprehensive data. Screens for various types of influenza would aid diagnosis compared to more limited tests on only single strains.

Currently there are no devices commercially available for personalized medicine and continuous blood monitoring diagnostics for early detection, prevention, and treatment of infectious, cerebrovascular and pulmonary diseases like sepsis, stoke, chest pain, or drugs of abuse. An essential clinical requirement is a POCd that detects the presence and monitors in real time the concentration of specific biomarkers in a patient's bloodstream, sweat, saliva or other bodily fluids. Many intensive care patients develop infections which are not detected quickly and often lead to sepsis or shock and ultimately a large mortality rate. POCd circumvent the lengthy processing hours and high costs accompanying conventional off-site laboratory assays being highly valuable for medical staff but also for first responders which need time-critical diagnoses.

These devices enable rapid diagnosis by first responders or medical staff for time-critical diagnoses, such as for indicating whether patients are presenting with cardiac symptoms. Tests have been developed for other indications, such as infectious diseases, drugs of abuse, cerebrovascular disease, that are intended to circumvent the lengthy processing hours and high costs accompanying conventional in-house laboratory assays. Current POC devices are single use only. While this is suitable for many applications, there is an unmet need for continuous monitoring devices.

There is a clinical need for a device that can monitor and detect the presence of infections in intensive care patients. Currently, many intensive care patients develop infections that are not detected quickly, often leading to sepsis or shock and resulting in a large mortality rate. There is a significant need for a device that can continuously track the concentration of specific protein markers in a patient's bloodstream that are indicative of an infection, for instance.

The field of biosensors holds the promise of satisfying these needs. A biosensor is a device capable of specifically detecting the presence of selected chemicals, biochemicals, biomolecules, pathogens, toxins, or explosives in a sample, by indirectly measuring its interaction with a target molecule present at the biosensor surface. The miniaturization, integration and redesign possibilities offered by biosensors and microfluidics compared to conventional laboratory assays suggest that biosensors will dramatically enhanced diagnostic capabilities and development of POCd.

Emerging applications of biosensors also include food, water testing, bio-defense and "white powder" detection, and veterinary testing. Some of these applications have unique needs such as the need for ultra-fast response time in conjunction with bio-defense measures, or very high sensitivity necessary in food or water testing, for example when detecting a very low number of $E.$ $coli$ colony-forming units. Typical water testing products use reagents that must be incubated in flasks for 18-24 hours or longer, and indicate pathogen presence by changing color of the media. While these products are very effective and sensitive, the 24-hour incubation time is problematic when the contaminated water is a public drinking water supply. A biosensor device that continuously monitors water contaminant would warn the authorities within minutes of actual contamination.

Bio-defense presents unique issues as governmental and military agencies search for ways to rapidly and interactively detect terrorist agents like anthrax, botulism, malaria, Ebola virus, ricin, and other potential agents. Expensive test kits are currently used by the US Postal Service that incorporate real-time PCR to amplify and analyze crude samples obtained from air or suspicious "white powder" on packages and envelopes.

In several illustrative examples, devices that are capable of detecting the presence of selected chemicals or biological substances include biosensors that interact directly with a sample molecule to provide a signal identifying the test molecule. Biosensors are often functionalized chemically to make them selective. The readout can be electrochemical, as is often the case for small molecules (e.g. glucose), or can utilize fluorescence or other optical techniques for molecules such as proteins or DNA.

The biosensors are classified as labeled when the detection involves the presence of fluorescent, radioactive tag or chemiluminescence, and the interaction and detection steps are completely independent or label-free when the interaction and detection are simultaneous. Based on the physical property that is modified during the molecular interaction, the label-free biosensors are classified as optical (when based on ellipsometry, interferometry, whispering gallery modes, total internal reflection, or surface plasmon resonance (SPR)), mechanical (when based on quartz micro-crystal, surface acoustic waves, or cantilever), electrochemical (when based on amperometry, calorimetry, potentiometry, or conductometry) or thermodynamical (based on isothermal titration calorimetry, or differential scanning calorimetry). Typical label-free biosensors can often operate in a continuous reading mode or can be used multiple times, which differs from conventional laboratory assays requiring bulk reagent handling, usually yielding only a one-time test result. Among the label-free biosensors, SPR sensors are a fast and simple technology widely used in life science research, drug discovery, toxicology, food, environmental and industrial testing, because it allows label-free, real-time quantitative monitoring of interactions between an analyte (e.g. protein, peptide, nucleic acid, polynucleotide or virus solution) and target molecules bound to a gold surface with the ability to specifically interact with that analyte.

Despite certain advantages over other technologies like mass spectroscopy or ELISA because it allows label-free real-time monitoring of molecular interactions, SPR suffers from certain disadvantages that have prevented its use in potentially much larger fields including bio-defense, forensics diagnostics, high-throughput drug discovery, or POCd for human and veterinary diagnostics.

SPR utilizes a phenomenon arising from the interaction of photons with a metal surface which embodies an oscillating charge-density (electron cloud). We can excite SPR on surfaces with many different textures: planar, grooved, waveguide-patterned or closed-packed spheres, using either incident electron beams or photons. To enhance this coupling, attenuated total reflection (ATR) through prism couplers, waveguides, or diffraction gratings can be used. Incident electron-beams are the oldest method. Waveguides and diffraction gratings date from the late 1950s. In the late 1960s Otto and Kretschmann independently discovered two more practical optical excitation configurations involving prism couplers which made the technique widely available.

This exciting condition is usually met at the interface between a dielectric (e.g. glass) and a metal (illustratively gold or silver). The charge density wave (the electron cloud) is driven into resonance with an electromagnetic wave (the incoming photons), and this coupling reaches a maxima at the interface and decays exponentially into both media. This coupling is a surface bound plasma wave (SPW) which cannot be excited directly by randomly incident photons at a planar metal-dielectric interface because the SPW propagates more slowly than photons in free space. On smooth planar surfaces (e.g. Otto and Kretschmann configurations), a SPW is a non-radiative, longitudinal, p-polarized, charge-density wave bound to the interface between a medium with real positive refractive index (a dielectric sample-medium) and a medium with a complex (negative real part) refractive index (an SPR-supporting metal).

An incident beam of p-polarized light (the electrical field perpendicular to the propagation vector and parallel to the incidence plane defined by the propagation vector and the vector normal to the interface) passes through the dielectric prism and falls on the metal film. By varying the angle of incidence of the incident photons we slow them down and bringing them into resonance with the SPW, thus reaching the resonance angle, when the evanescent wave in the prism excites the SPW (FIG. 1). The light's p-polarization and incidence at the resonance angle are both essential to SPW excitation through a prism coupler. Incident p-polarized light optimally excites the SPW, which is itself p-polarized. A resonance conditions exists because the parallel-to-interface component of the incident-photon wave-vector matches SPW-vector and the energy of the photons transfers to the SPW, extinguishing the reflected beam. Owing to the strong concentration of the electromagnetic field in the dielectric (an order of magnitude higher than that in typical evanescent field sensors using dielectric waveguides) the propagation constant of the SPW, and consequently the SPR realization, is very sensitive to variations in the optical properties of the dielectric adjacent to the metal layer supporting SPW, namely the refractive index of the dielectric media which may be determined by optically interrogating the SPW. The thickness of the region of sensitivity varies with the wavelength off the applied energy, but is typically about 500 nm for wavelengths in the visible light range. The refractive index is modified by the presence of materials or impurities at the surface. This is the fundamental effect that can be used to identify binding activity at the surface.

Only few metals are can provide the negative sign dielectric constant. They have a resonant mode at which the constituent electrons resonate when excited by electromagnetic radiation having the right wavelength. Gold, in particular, has a spectrum with a resonance at visible wavelengths around 510 nm. In the case of the attenuated total reflection in prism couplers, the evanescent wave is sensitive to changes in the refractive index at the metal surface in contact with the media within approximately 200-400 nm of the surface, enhanced by the presence of a surface plasmon wave (SPW) (FIG. 1). Interactions between a bound substrate and a sample can thus be probed, measuring small variations in the reflection angle at maximum SPR production.

This effect can be harnessed to study binding between molecules, such as between proteins, RNA and/or DNA, or between proteins and pathogens (e.g. viruses, bacteria, fungi, and the like). In an illustrative exampler a surface functionalized with a specific antibotic (e.g. target molecule) will probe selectively for one antigen (e.g. antigen A) and discriminate specific binding from non-specific binding with other antigens (e.g. antigen B). That is, antigen A will be detected, but the weaker interactions between the functionalized protein bound to the surface and another antigen, say antigen B, can be distinguished by the corresponding kinetic profile.

Most commercial SPR instruments comprise a sample injection/rinsing device, a sensor surface made of a thin layer of gold (~50 nm) coated on a glass slide that is brought in contact with a refractive-index matching semispherical dielectric prism. The gold layer is functionalized with target molecules that specifically bind to the analyte of interest. These commercial instruments further comprise a polarized light source, a photo-detector array, and various collimations and filtering optics on a goniometric mount as sketched in FIG. 1.

Using a semispherical prism, the angle of incidence at the dielectric/air interface is the same as at the first air/dielectric interface where the ray from the light source enters the prism. At the critical incidence angle (surface plasmon resonance angle, $\Phi_{SPR}$) at which incident photons couples to the SPW in the metal film the reflectivity of the film decreases more than 90% creating an evanescent plasmon field which is localized at the metal surface away from the glass. The evanescent wave's properties depend on the optical properties of the medium (e.g. biomolecules) in contact with the free metal surface of the sensor. Subtle changes in the refractive index of the medium, such as those associated with molecular absorption onto the surface induce detectable changes in the $\Phi_{SPR}$. The goniometric mount then adjusts the detector position to find this new angle and thus measures the change in SPR angle which correlates to the interaction kinetics of the antigen in solution with the target molecules fixed on the surface.

These types of SPR devices have a number of inherent limitations involving sensitivity, sample-sensing size, instrument size, complexity, and cost. Existing commercial instruments require large, complex, and delicate moving parts in order to optimize the incident beam and detector positions. The goniometric mount is relatively big and very delicate. The light source itself must provide polarized light. Typical sensitivity limits are on the order of $10^{-6}$ refractive index units corresponding to an angular resolution of 0.1 millidegree which can detect targets with a mass distribution of 1 pg/mm$^2$ of adsorbed molecule and a size of at least 200 Da, but is not sensitive enough to provide useful detection for bio-terrorism agents in concentrations of 0.01 parts per billion as required by certain government standards. The typical planar sensor footprint is in the range of a few mm$^2$ ($\frac{1}{16}^{th}$ mm$^2$ in the Biacore Flexichip and 2.2 mm$^2$ in the Biacore 3000) which creates a technical constraint on the ability to miniaturize the classical SPR sensors. A larger sensor area means that more test fluid must be provided to flow over the planar sensor. Moreover, the constraints on accuracy also require more test fluid to provide sufficient molecules or microparticles to be detected. Because of an SPR sensor's macroscopic size, arrays of sensing elements for multiplexed analysis require sample volumes too large for most technologies used for analytical integration. All of these limitations of conventional planar sensors reduce the throughput capability of the sensors. Overall the complexity of classical SPR instruments matches to those of a tabletop spectrometer which implies a high cost, typically on the order of several hundred thousand dollars.

BACKGROUND AND SUMMARY

Figure 1:
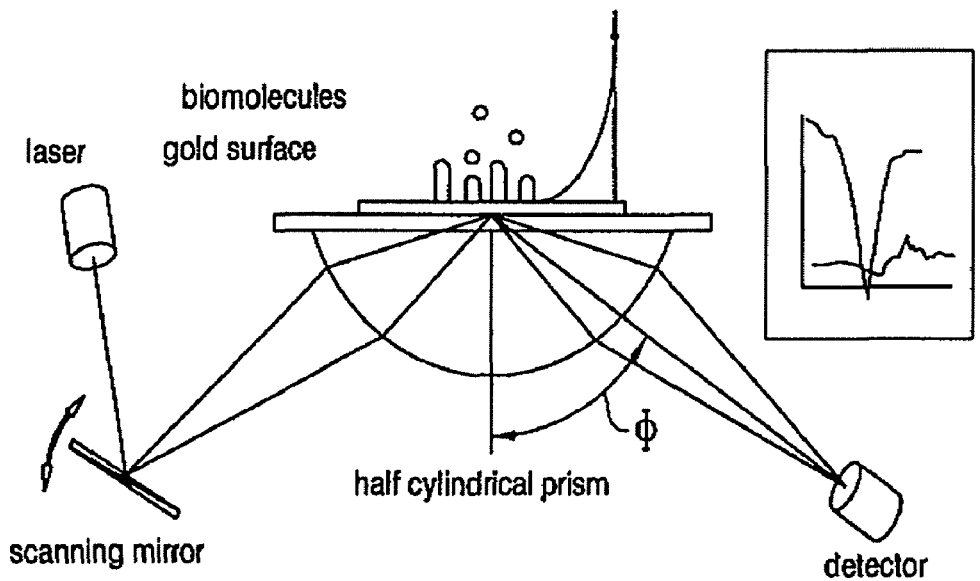
FIG. 1 is a schematic representation of the operation of a classic planar SPR sensor.

Classic planar SPR sensors are a fast and simple technology widely used in life science research, drug discovery, toxicology, food, environmental and industrial testing, because it allows label-free, real-time quantitative monitoring of interactions between an analyte (e.g. protein, peptide, nucleic acid, polynucleotide or virus) and a target molecule bound to a gold surface that specifically interacts with the analyte. Despite certain advantages over other technologies like mass spectroscopy or ELISA because it allows label-free real-time monitoring of molecular interactions, classical SPR suffers from disadvantages that have prevented its use in potentially much larger fields including bio-defense, forensics diagnostics, high-throughput drug discovery, or point-of-care testing (POCT) for human and veterinary diagnostics.

Evanescent-wave sensors using SPR techniques for biomolecular interaction analysis, for instance, provide several advantages, including non-intrusiveness, real-time monitoring of the binding of target analytes, ligands or molecules and label-free conditions. A mechanism to increase the sensitivity of SPR sensors while reducing their size and eliminating the often fragile mechanical and optical components that add bulk to the SPR instruments, without increasing the response time is very desirable, especially in the fields of medical diagnostics, drug screening, biomedical research, and bioanalysis. In accordance with one aspect of the present invention, the propagating surface plasmon wave (SPW) is replaced with a stationary surface plasmon wave or, in other words, the sensitivity of the SPR sensor is enhanced by adding shape resonance to otherwise dissipating SPW. Such a stationary SPW (SSPW) will travel across the active surface a number of times proportional to the quality factor of the resonance, thus increasing the probability of interaction between the wave and the binding agent binding at the sensor's surface.

The circulation of light within highly symmetric microscopic structures often involves such shape resonances. For dielectric spheres 10-100 μm in size, a particular class of resonances occurs known as whispering gallery modes. The term stems from similarities with the phenomenon of circumferential guiding of faint sounds along the walls of the gallery of St. Paul's Cathedral in London. Bioanalytical and spectroscopic applications can take advantage of the characteristic of strong surface localization and high quality factors of whispering gallery modes in dielectric microspheres and liquid droplets. However, the whispering gallery modes gradually lose their surface localization properties as the microsphere size decreases, generally rendering whispering gallery modes ineffective in a microsphere environment (less than 10 μm in diameter).

For submicron sizes (i.e., less than 1 μm in diameter), one way to maintain light confinement is to coat the sphere with a SP-supporting metal film. One characteristic of such a submicron sphere coated with a metal film is that at certain diameters the total internal reflection angles associated with cavity modes may coincide with the critical SPR angle for the metal film, thus resulting in a more efficient form of SP excitation on geometrically symmetric surfaces. This feature eliminates the need for the polarized light source, optical alignment and mechanical scanning found in prior sensors, and allows relaxation of the stringent geometric conditions imposed on planar sensors.

The present invention comprises a novel sensor that may be optimally used in combination with micro-fluidic systems. Measurements of (bio)-chemical concentrations and kinetics of reactions inside a confined space such as a micro-fluidic device are very difficult. The present invention contemplates a sub-micron dielectric sphere covered with a metal which supports surface plasmons, e.g. Au, Ag or Cu. This SPR shows a strong enhancement in transmission of certain wavelengths due to the periodic boundary conditions created by the geometry of the sensor element coupled with surface plasmons induced in the metal shell. This inventive sensor is sensitive to small changes of the refractive index of the material at the very surface of the sensor (i.e., within about 300 nm) and is much more sensitive than prior far-field sensors and detection techniques.

Thus, the present invention contemplates a micro-cavity device that utilizes stationary surface plasmon waves enhanced by geometric or shape resonances. For the purposes of the present disclosure, this device will be referred to herein as a Micro-cavity Surface Plasmon Resonance (MSPR) sensor. In the following description, a spherical cavity resonator has been selected, but it is understood that other symmetric geometric shapes may be used that are capable of sustaining boundary conditions for the stationary plasmon resonance wave to travel across the active surface.

Thus, in one aspect of the invention, the MSPR replaces the propagating plasmon wave associated with traditional SPR sensors with a stationary wave that travels across the active surface of the sensor element. In order to achieve this near-field coupling the dielectric cavity resonator is coated with an SPR-supporting metal of a particular thickness. This metal layer, together with the refractive index of the cavity resonator material, establishes a resonant frequency (or frequencies) for the cavity resonator sensor element. The dimension of the sensor element is then determined in relation to this resonant frequency. In particular, in one aspect, the sensor element is sized at about the wavelength of the resonant frequency.

In accordance with the invention, the MSPR sensor element is made by mounting a dielectric core (e.g. nanosphere, nanoparticle, nano-bead) on a light transmissive substrate, such as glass, but it can be any transparent material. The substrate and the nanosphere are coated with an SPR-supporting material, such as gold. A feature of the invention is the sub-wavelength sized nanoaperture or pinhole, free of the coating material, generated at the interface between the nanosphere and the substrate. The size of this pinhole is also calibrated to the resonant wavelength for the sensor, so that the pinhole diameter is less than that wavelength. The MSPR sensor further requires a light source directed at the sensor dielectric core that is operable to induce the stationary SPW resonances. Thus, the light source could provide light at the resonant wavelength for the MSPR sensor resonances, and may be monochromatic at the desired wavelength. In another embodiment, white, chromatic light can be used. The light may be directed at the coated surface of the core or at the pinhole, with a detector positioned to receive light transmitted through the MSPR sensor.

Due to its small size the MSPR sensors of the present invention can be incorporated into micro-fluidic devices in order to get information about the (bio)chemistry occurring inside the micro-fluidic channel. These devices will allow manufacture of compact, disposable sensors which can rapidly detect and quantify multiple (bio)chemicals or pathogens, as well as their concentrations, using small sample volumes. Thus, the MSPR sensor of the present invention will have important applications in medical diagnostics, prevention and therapeutics, including but not limited to, the diagnosis and treatment of sepsis, in laboratory instrumentation for monitoring chemical reactions and in detection of biochemical and biological hazards (e.g. bioterrorism or pollution).

In general the MSPR sensor of the present invention can be applied to applications in which interaction with (bio)chemicals changes the refractive index of the bulk media in contact with the surface of the sensor. In the case of a functionalized detector, the present invention can be used in applications in which the chemical interaction causes changes in thickness or compactness of the self-assembled monolayer that covers the surface of the MSPR sensor and can chemically interact with the analytes or ligands. Some general (not limiting) applications of the MSPR sensor of the present invention include:

1. A method to functionalize the detectors inside microfluidics devices.
2. Applications detecting molecular species interactions inside micro-fluidic channels.
3. Applications detecting small molecular species.
4. Determination of specific binding between molecules.
5. Measurements of affinity constants and dissociation constants of specific molecular pairs, e.g., ligand-receptor pairs, ligand-antibody pairs.
6. Determination of chemical concentrations of analytes inside a micro-fluidic device.
7. Determination of diffusion coefficients of chemicals in restricted geometries.
8. Detection and quantization of molecular species in real time in bodily fluids, like, but not limited to, blood plasma, sweat, saliva, tears, seminal and vaginal fluids, cerebrospinal and peritoneal fluid, mucus, sebum, gastric juice, and urine.
9. Detection and quantization in real time of (bio)chemical or biological hazards in air, water and food.
10. Detection in real time of molecular species to control release of therapeutic agents, for instance to control disease states.
11. Detection in real time of hazardous waste or industrial chemicals in air or water.
12. Detection in real time of pathogens (e.g. viruses, bacteria, fungi, and the like.) in blood plasma and other body fluids.
13. Determination of blood chemistry in human and veterinary applications.
14. Detection of explosives or explosives/firearms residue.
15. Detection of DNA and/or RNA, or detect binding or DNA/RNA with certain proteins, oligonucleotides, or peptides on the order of single cells or at most a few cells.
16. Detection in real time of single cell secretion or tissue level secretion
17. Process analysis and/or control for chemical or biochemical industrial processes.

One benefit of the present invention is the elimination of the complicated optics required for conventional planar sensors. For instance, the MSPR sensor of the present invention can use diffuse light from a low-cost light source. The light need not be polarized, filtered or directed. The present invention eliminates the need for fragile and bulky optical alignment components, such as the goniometric mounts in some prior systems.

A further benefit of the MSPR sensor of this invention resides in its capability to be integrated into a small package, or chip. The inventive MSPR sensor allows the light source and the light detector to be positioned very near the MSPR sensor array, thereby significantly reducing the profile of the present MSPR sensor over prior planar sensors.

It is one object of the invention to provide a micro-sensor that is capable of detecting the presence of target analytes, ligands or molecules in a fluid. A further object is to enhance the sensitivity and speed of detection of the micro-sensor.

It is another object of the invention to provide implantable or wearable devices incorporating miniaturized microcavity-surface-plasmon-resonance sensors (i.e. MSPR sensors, MSPRS) integrated to microfluidic networks for use in human and veterinary diagnostics as point-of-care-testing (POCT) devices. The wearable or implantable sensor device contemplated herein can be used to monitor the health status of a patient. It is recognized that wearable POCT devices (w-POCT) and implantable POCT (i-POCT) devices can be used in personalized medicine. The contemplated devices are useful for real-time, continuous diagnostic blood monitoring for early detection of (and therefore possible amelioration of), monitoring the progress of, and monitoring the treatment of disease in a patient. Illustrative diseases are local and systemic infections, sepsis, stoke, cardiovascular diseases, pulmonary diseases, chest pain, cancer, diabetes, metabolic syndrome disease, hyperlipidemia, inflammatory diseases, graft versus host disease (often resulting in organ transplant rejection), and other conditions and/or diseases causing a change in an amount of one or more analytes in the blood of a patient. As used herein, the term "realtime," applied to detection, measurement or monitoring, shall be understood to mean that the measurement, monitoring, or detection of one or more analytes occurs in a time period such that the measurement, monitoring or detection remains useful for the purpose for which it is being gathered.

It is contemplated that both implantable and wearable devices can be connected directly to the blood stream of a patient requiring monitoring, e.g. postoperative and post-trauma patient, to monitor the onset and progress of certain diseases or conditions. The biosensors can be functionalized to detect blood components (i.e. blood markers) whose binding to the surface of the biosensors produces a detectible change in the signal recorded by the device. Wearable devices can be attached to patient's skin (e.g. chest, wrist, waist, thigh, ankle, forearm, and the like) by using an adhesive pad or band, and the like. The monitoring device can be affixed to a tissue having a low density of pain-sensing nerves, such as the forearm or thigh. In one embodiment, a sharp needle or micro-needle attached to the device pierces the skin and connects the device to the blood stream. Through this connection blood can migrate or flow into the device. It is appreciated that movement of blood or other fluids into the device may be the result of capillary action, diffusion, or a pressure difference between the blood system or fluid source and the device. Use of the combination of MSPR sensors integrated with microfluidic elements in the device allows results to be obtained from small amounts of blood (e.g. a couple of droplets in an hour). In an attached or wearable MSPR sensor device the path from the blood stream or fluid source to the MSPR sensors is so short that the target analytes (blood markers) can be monitored in real time. It is appreciated that implantable devices can be encapsulated in one or more known biocompatible materials. It is further appreciated that implantable devices may be placed next to an organ or tissue of interest, thus being capable of monitoring localized, very low concentrations of analytes (e.g. blood markers). In one embodiment the wearable or implantable device connects wirelessly to a POCT monitoring or recording station and provides a notification to the medical staff or patient when the analyte (i.e. blood marker) concentrations reach levels set by the monitoring software, the patient or medical personnel.

In one embodiment, the monitoring device can be affixed to a tissue having a relatively low density of pain-sensing nerves, such as the forearm or thigh.

Yet another object of the present invention is to provide a sensor that may provide high throughput detection in micro-environments. Other objects and benefits of the invention will become apparent from the following description.

DETAILED DESCRIPTION

Several illustrative embodiments of the invention are described by the following enumerated clauses:

1. A wearable device for monitoring the concentration of one or more target analytes, ligands, or molecules in a body fluid comprising:
    a conduit adapted to connect to the patient's bodily fluid; and;
    a sensor chip, wherein the sensor chip comprises
    a light transmissive substrate;
    a housing formed of a light transmissive material and defining at least one fluid cavity in communication with at least one fluid inlet for receiving the body fluid and at least one fluid outlet;
    one or more micro-cavity surface plasmon resonance (MSPR) sensors mounted on a surface of the light transmissive substrate;
    a light source arranged to direct light toward the MSPR sensors; and
    a detector arranged relative to the one or more MSPR sensors to detect their emitted light;
    wherein the one or more MSPR sensors are mounted randomly or non-randomly over a spatial domain of said surface;
    an exposed surface of each MSPR sensor is functionalized with a surface treatment, or a surface coating of a material capable of binding with the one or more targets to be detected;
    each MSPR sensor includes a light transmissive core formed in a geometric shape that can sustain periodic boundary conditions for a stationary surface plasmon waves to travel across the outer surface thereof; and a pinhole is defined at the interface between each MSPR sensor and the substrate; and
    the conduit is in communication with at least one of the fluid inlets.

2. The wearable device of clause 1 wherein the light source is at least one light-emitting device.

3. The wearable device of clause 1 wherein the light detector includes an array of pixels, each pixel operable to generate an output in response to the detection of light at said pixel.

4. The wearable device of clause 1, further comprising a micro-fluidic channel.

5. The wearable device of clause 1, further comprising a micro-fluidic pump.

6. The wearable device of clause 1, wherein said fluid inlet includes at least a micro-fluidic valve.

7. The wearable device of clause 1, wherein said housing further defines at least one additional fluid inlet in communication with said cavity.

8. The wearable device of clause 7, wherein said additional fluid inlet includes at least a micro-fluidic valve.

9. The wearable device of clause 1, wherein at least one of said fluid inlets includes a filter for controlling fluid quality in said cavity.

10. The wearable device of clause 3 wherein there is a plurality of MSPR sensors where the plurality of MSPR sensors are randomly or non-randomly distributed over the array of pixels.

11. The wearable device of clause 10 wherein there is a plurality of targets.

12. The wearable device of clause 11 wherein the plurality of MSPR sensors are in a plurality of groups where each MSPR sensor in a group is commonly functionalized with a surface treatment, or a surface coating of a material capable of binding with one of the targets.

13. The wearable device of clause 12, wherein the groups of commonly functionalized MSPR sensors are arranged in a plurality of columns wherein in each column contains one of the groups of commonly functionalized MSPR sensors; and said housing defines a flow channel over each of said plurality of columns.

14. The wearable device of clause 10 wherein the body fluid is blood.

15. The wearable device of clause 14 wherein the targets are biomarkers for a disease or condition.

16. The wearable device of clause 15 wherein the targets are selected from the group consisting of blood markers for sepsis, cytokines, growth factors, and tumor markers.

17. The wearable device of clause 16 wherein the targets are interleukin-1, interleukin-6, interleukin-10, interleukin-13, transforming growth factor-$\beta$, and tumor necrosis factor-$\alpha$ or any other biomarkers.

18. The wearable device of clause 1 further comprising a strap, an adhesive pad, or a combination thereof.

19. The wearable device of clause 1 further comprising a system of communication with a remote station.

20. An implantable device for monitoring the concentration of one or more target analytes, ligands, or molecules in a body fluid comprising:
    a conduit adapted to connect to the patient's bodily fluid; and;
    a sensor chip, wherein the sensor chip comprises
    a light transmissive substrate;
    a housing formed of a light transmissive material and defining at least one fluid cavity in communication with at least one fluid inlet for receiving the body fluid and at least one fluid outlet;
    one or more micro-cavity surface plasmon resonant (MSPR) sensors mounted on a surface of the light transmissive substrate;
    a light source arranged to direct light toward the MSPR sensors; and
    a detector arranged relative to the one or more MSPR sensors to detect emitted light;
    wherein the one or more MSPR sensors are mounted randomly or non-randomly over a spatial domain of said surface;
    an exposed surface of each MSPR sensor is functionalized with a surface treatment, or a surface coating of a material capable of binding with the one or more targets to be detected;
    each MSPR sensor includes a light transmissive core formed in a geometric shape that can sustain periodic boundary conditions for a stationary surface plasmon waves to travel across the outer surface thereof; and a pinhole is defined at the interface between each MSPR sensor and the substrate; and
    the conduit is in communication with at least one of the fluid inlets.

21. The implantable device of clause 20 wherein the light source is at least one light-emitting device.

22. The implantable device of clause 20 wherein the light detector includes an array of pixels, each pixel operable to generate an output in response to the detection of light at said pixel.

23. The implantable device of clause 20 further comprising at least a micro-fluidic channel.

24. The implantable device of clause 20, further comprising a micro-fluidic pump.

25. The implantable device of clause 20, wherein said fluid inlet includes at least a micro-fluidic valve.

26. The implantable device of clause 20, wherein said housing further defines at least one additional fluid inlet in communication with said cavity.

27. The implantable device of clause 26, wherein said additional fluid inlet includes at least a micro-fluidic valve.

28. The implantable device of clause 20, wherein at least one of said fluid inlets includes a filter for controlling fluid quality in said cavity.

29. The implantable device of clause 22 wherein there is a plurality of MSPR sensors where the plurality of MSPR sensors are randomly or non-randomly distributed over the array of pixels.

30. The implantable device of clause 29 wherein there is a plurality of targets.

31. The implantable device of clause 30 wherein the plurality of MSPR sensors are in a plurality of groups where each MSPR sensor in a group is commonly functionalized with a surface treatment, or a surface coating of a material capable of binding with one of the targets.

32. The implantable device of clause 31, wherein the groups of commonly functionalized MSPR sensors are arranged in a plurality of columns wherein in each column contains one of the groups of commonly functionalized MSPR sensors; and said housing defines a flow channel over each of said plurality of columns.

33. The implantable device of clause 29 wherein the body fluid is blood.

34. The implantable device of clause 33 wherein the targets are biomarkers for a disease or condition.

35. The implantable device of clause 33 wherein the targets are selected from the group consisting of blood markers for sepsis, cytokines, growth factors, and tumor markers.

36. The implantable device of clause 35 wherein the targets are interleukin-1, interleukin-6, interleukin-10, interleukin-13, transforming growth factor-$\beta$, and tumor necrosis factor-$\alpha$.

37. The implantable device of clause 20 wherein the implantable device is encapsulated in a biocompatible material.

38. The implantable device of clause 20 further comprising a system to attach the device to an organ, a specific tissue, or any desired location inside the body.

39. The implantable device of clause 20 further comprising a system of communication with a remote station.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
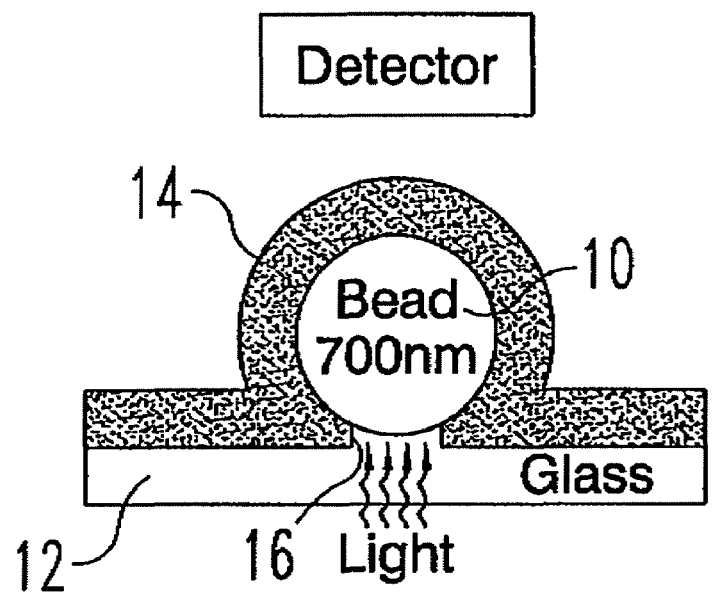
FIG. 2 is an enlarged schematic representation of sub-micron surface plasmon resonance sensor in accordance with one embodiment of the present invention.

In accordance with one embodiment of the invention, a resonant microcavity sensor (MSPR) comprises a spherical dielectric nanoparticle 10 supported on a substrate 12, as depicted in FIG. 2. The nanoparticle is coated with a layer 14 of SPR-supporting material, such as gold, that is excited through a near-field pinhole 16 defined between the nanoparticle and the substrate. The light scattered from the coated nanoparticle exhibits strong spectral resonances associated with the coupling of surface-plasmon modes. These resonances can be used for sensing purposes, like the surface-plasmon resonances used for studies of molecular binding on planar surface-plasmon sensors, but with the advantages of a submicron footprint, a million-time smaller and the high quality factors of nanospherical resonators, yielding a 100-fold improvement in sensitivity over prior SPR sensors.

The improvement in overall device dimensions is accomplished because the MSPR sensor of the present invention relies upon light transmission rather than reflection. The pinhole 16 at the interface between the nanoparticle 10 and the substrate 12 has a diameter less than the wavelength of the light exciting the MSPR resonances, so only near-field evanescent-wave light will pass through the pinhole. However, the light passing through the pinhole is, by itself, insufficient for a sensor to function. Thus, in accordance with the present invention, the addition of the spherical resonant cavity above the pinhole converts this near-field light to far-field light that can be readily sensed or observed. The symmetrically shaped nanoparticle over the pinhole allows the transmission of light through the pinhole in and out of the resonant cavity to produce easily observed light transmission on the other side of the nanoparticle. In one illustrative embodiment, a laser diode provides light at a wavelength of about 600 nm, so the pinhole 16 has a diameter less than the wavelength, and more preferably a diameter of less than about 300 nm. In certain examples described herein, the pinhole diameter established at the contact between the MSPR dielectric core and the light transmissive substrate is in the range of 100-200 nm, or around 150 nm, for a dielectric nanoparticle with a diameter of 770 nm. It is contemplated that smaller pinhole diameters will be generated for smaller dielectric nanoparticle diameters.

As expressed above, the MSPR sensor of the present invention does not require any complicated optics associated with prior SPR devices that rely upon surface plasmon waves propagating along a planar, flat substrate surface. In particular, the MSPR sensor shown in FIG. 2 does not require a light source on a goniometric mount or collimation, filtering and polarizing optics for evaluating changes in any SPR angle associated with prior art devices like the device depicted in FIG. 1. Instead, the MSPR sensor of the present invention may be illuminated by light transmitted substantially perpendicular to the substrate 12 into the MSPR sensor. Moreover, contrary to the prior art devices of FIG. 1, the light source may be situated on either side of the substrate, as explained in more detail herein.

Furthermore, this freedom from the optical and goniometrical constraints of the prior devices allows the MSPR sensor of the present invention to utilize a wide range of light sources at a wide range of frequencies. For the purposes of the present disclosure, reference to "light" is not limited to visible light wavelengths. Thus, the light source (or more broadly the energy source) may provide light in the ultraviolet, visible and infrared spectral ranges. Although wavelengths outside the UV and IR ranges are not presently known to be used in surface plasmon sensors, the invention does not exclude any later discovered energy wavelengths that observe the plasmon resonance characteristics of the present invention.

Example 1

Fabrication of an MSPR Sensor

The following is a description of one method for laboratory fabrication of the MSPR sensor shown in FIG. 2. It is understood that other fabrication techniques are possible for specific applications. It is further understood that the immediately following description is principally for a sensor adapted for research use, rather than for commercial application, although the same principles may be applied to produce a commercially viable sensor.

Microscope cover glasses No. 1, 30×24 mm, 156 µm thick, are scored with a diamond and broken into four equal pieces. Also, microscope slides, 25 mm×75 mm are scored and broken into two equal pieces. The slides and cover glasses (items 12, 62 and 64, respectively, in FIGS. 2 and 4) are cleaned using a modified version of the well-known RCA cleaning protocol ($H_2O_2$:$H_2O$:$NH_4OH$-2:1:2, warmed to 70° C.) followed by rinsing in DI water and drying with $N_2$. The cleaned cover glasses are placed in a dry atmosphere in a bell jar that can be connected to a mechanical pump in order to create low vacuum inside. Diluted solutions of polystyrene nanospheres, about $10^4$ particles/μL with diameters 360 nm, 480 nm and 770 nm, are prepared in advance and 50 μl of each solution is dispensed on each piece of cover glass. Due to the cleaning solution, the surface of the glass turns hydrophilic. After 2-3 hours of exposure to the vacuum in the bell jar (~1 torr) the liquid dries out and the nanospheres remain fixed on the cover glass, forming a random, mono-dispersed layer of particles. The concentration is chosen so the average distance between neighboring nanospheres is sufficiently large (at least 10-50 μm) to avoid optical cross talk. These samples are sputter coated with a 150 nm layer of gold by exposing them for eight minutes to argon plasma.

Figure 3:
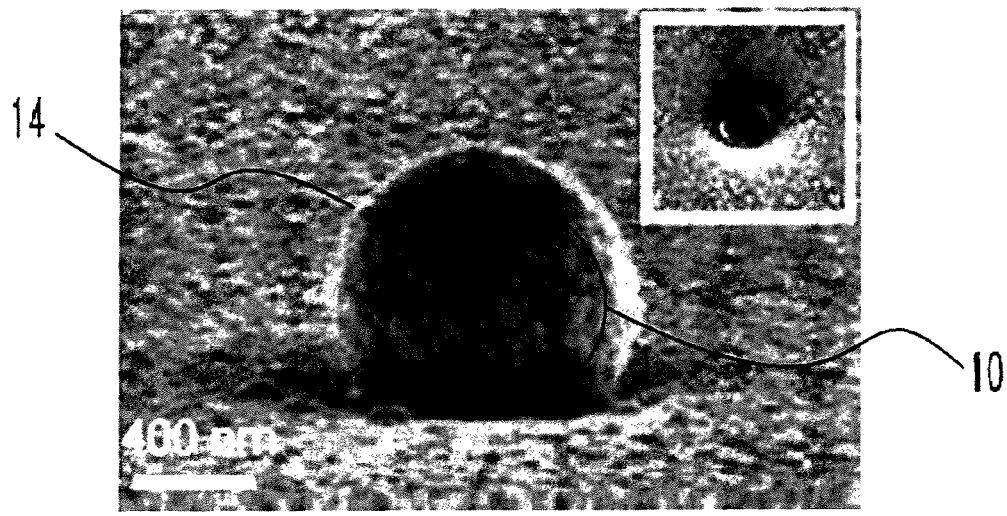
FIG. 3 is an electron-microscopic image of sub-micron surface plasmon resonance sensor (e.g. a MSPR sensor) fabricated according to the present invention.

An electron-microscope image of a 771 nm polystyrene nanosphere, sputter coated with 150 nm gold on a glass substrate is shown in FIG. 3. It is understood that the sputter coating is capable of producing the pinhole interface between the nanosphere 10 and the glass substrate 12—in other words, the pinhole is substantially free of the coating material. For several wavelengths, the light emitted by the MSPR sensors of the present invention when illuminated with white light from underneath the MSPR sensors is about 100 times more intense than the light transmitted through a flat gold layer of the same thickness.

Example 2

Fabrication of a Micro-Fluidics Chip with MSPR Sensors

Figure 4:
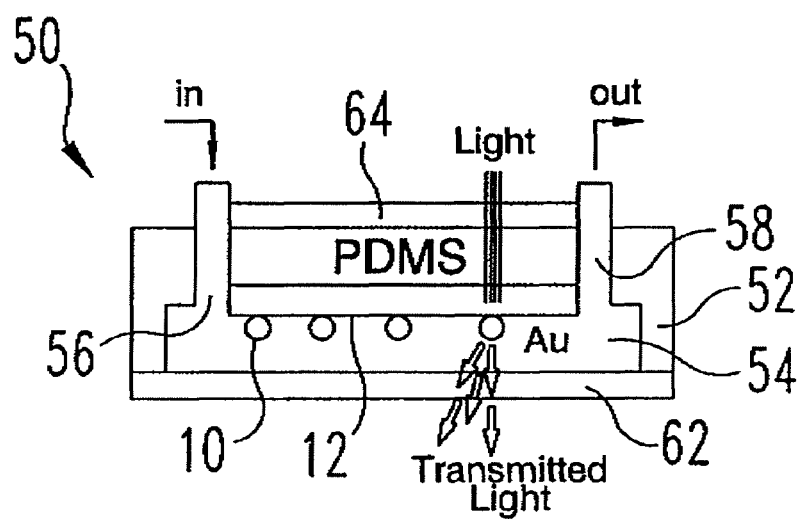
FIG. 4 is a schematic view of a micro-fluidic chip utilizing the sub-micron surface plasmon resonance sensor according to the present invention.

According to another embodiment of the invention, a process is provided for the fabrication of the sensors of the present invention in a micro-fluidic chip, such as the chip 50 shown in FIG. 4. Variations of the same protocol will allow fabrication of more complex sensors. In this process, the MSPR sensors are mounted within a housing, which in the preferred embodiments is in the form of a micro-chip. The micro-chip format for the MSPR sensor allows the sensor to be readily integrated into micro-systems, such as a micro-fluidics chip described herein.

In accordance with this embodiment, the fluidics chip is made using photolithographic technology and chip replica molding in polydimethylsiloxane (PDMS). The fluidics devices are fabricated using the negative-tone photoresist SU-8 as a master to cast PDMS channel structures. The master substrates are 50 mm×50 mm glass slides. The substrates are cleaned in HCl:HNO3 (3:1), rinsed with de-ionized water, dried with $N_2$, sonicated in methanol and acetone (2:1), and again dried with $N_2$. The master is made with one SU-8 2070 photoresist layer about 100 μm thick. The photoresist is spin coated on the glass substrate at 3,000 rpm for 30 sec and ramped at 120 rpm/sec. After pre-baking on a hot plate for 15 minutes at 65° C. and 90 minutes at 95° C., the photoresist is then exposed to UV light of 365 nm wavelength. The UV exposure system is equipped with a high pressure Hg arc lamp filtered to pass 360±45 nm, and the exposure dose is 300 mJ/cm². The exposed photoresist is post-baked on the same hot plate for ten minutes at 65° C. and 30 minutes at 95° C. and cooled to room temperature. The master is then developed for ten minutes, rinsed with 2-propanol, and dried with $N_2$.

The fluidic pattern is transferred to the photoresist through a photomask drawn using AutoCAD2004 LT and printed on a transparency. The fluidic pattern in the illustrated embodiment represents a rectangular fluidic chamber 54 (15 mm×10 mm) having two identical channels, an input channel 56 and an output channel 58 (5 mm wide and 10 mm long). The fluidic chamber depth is limited by the depth-of-field of the 60× immersion oil microscope objective used to analyze the sensors. The fluidic chamber has to accommodate the substrate 12 (156 μm thick in the present example) holding the nanosphere 10 covered with the gold layer 14 shown in FIG. 2. To provide a fluidic chamber having a depth of about 300 μm, the fluidic chamber part of the master is modified by binding a piece of glass substrate 62 identical to that holding the nanospheres. Preferably, the substrates 12 and 62 have substantially the same optical properties and thickness.

The silicon elastomer kit contains a polymer base and curing agent that are mixed in a 10:1 ratio for five minutes. A tape barrier is placed around the mold to hold the elastomer mixture, and the elastomer is poured onto the master. The PDMS in the mold is placed under low vacuum (~1 torr) for one hour to enhance fluidic pattern replication and cured by heating at 120° C. for twenty minutes. The PDMS substrate is then separated from the master, and access holes for fluid connections to the channels are punched through the elastomer with a 16 G needle.

At the bottom of the fluidic chamber of the PDMS chip 50 the substrate 12 holding the nanospheres covered with gold is attached to the ceiling of the fluidic chamber 54 of the PDMS chip 50 with a drop (50 μL) of PDMS. The substrate is placed with the sensors facing away from the PDMS mold and exposed to the inside of the fluidics chamber. The binding is final after ten minutes baking at 90° C.

The fabricated PDMS substrate and a 25 mm×50 mm No. 1 cover glass 62 are then permanently joined after being exposed to air plasma for 40 seconds prior to contact. To increase the rigidity of the chip 50 and to eliminate mechanical perturbations in the flow, a half microscope slide 64 (25 mm×38 mm) is permanently bound on top of the chip using the same air plasma technique. In this example, the depth of the fluidic chamber is estimated to be less then 50 μm in one specific embodiment so that the sensors can be brought into the focus of a 60× oil immersion objective with a working distance of 200 μm.

Example 3

Operation of the Micro-Fluidics MSPR Sensor Chip

In one method of using the micro-fluidics chip 50 (FIG. 4), fluid connections from the fluidics chip to fluid reservoirs, such as a syringe or a fluid pump, are made using 1.6 mm OD polypropylene tubing. The flows are controlled by adjusting the height of the reservoir connected to the input channel 56 relative to the height of the reservoirs connected to the output channel 58, or controlled by the fluid pump, so that a stable flow of about 1 μL/s achieved. After the chip is connected to the reservoirs it is placed on a piezo-driven stage capable of motion in all three directions (3D) that can position the sensor chip in space with a precision of 10 nm. The whole ensemble is placed under an inverted microscope and microscope objectives of 40× and 60× are used to collect and analyze the signal coming from a single sensor.

Figure 5:
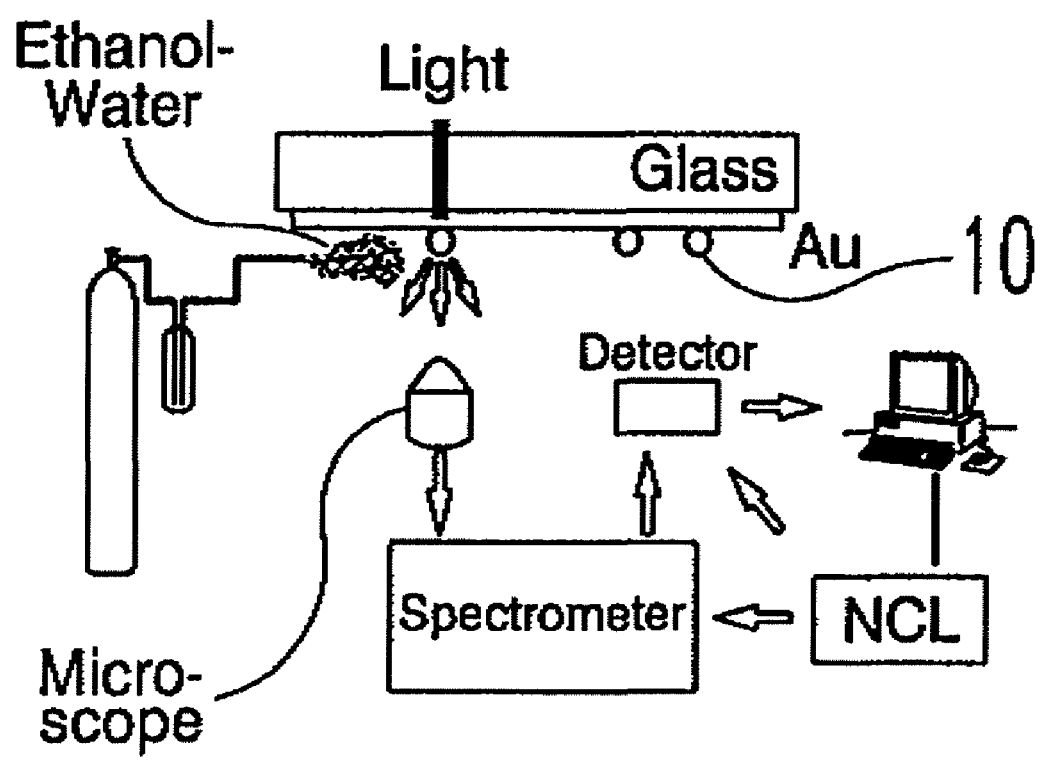
FIG. 5 is a schematic representation of an experimental set-up for evaluating the performance of a sub-micron surface plasmon resonance sensor according to the present invention.

The functionality and sensitivity of the MSPR sensor 50 may be evaluated using an experimental set-up shown in FIG. 5. In one experiment, the sensitivity of the sensor to vapors is tested. The substrate holding sensors is placed on a 3D-piezo-driven stage that can position the sensor in space with a precision of 10 nm. The whole assembly is placed on the stage of an inverted microscope and microscope objectives of 40× are used to collect and analyze the signal coming from a single sensor. The light coming from the sensor is fed through a parallel port into a monochromator driven by a data acquisition interface unit. Spectra in the visible range from 400 nm to 800 nm may be recorded on a PC with a resolution of 2 nm and 1 sec detector integration time.

Figure 6A:
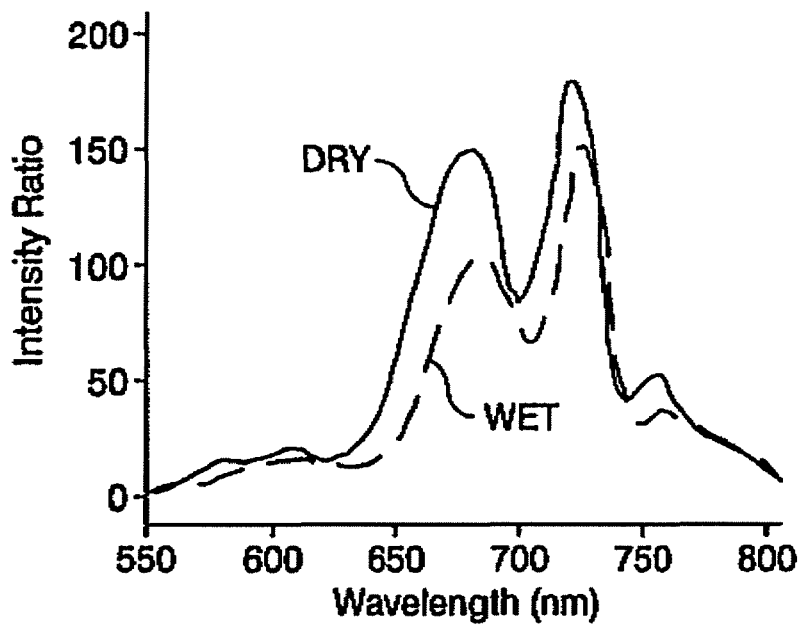
FIGS. 6a and 6b are graphs of the spectral and reproducibility performance of the sub-micron surface plasmon resonance sensor in the experimental set-up shown in FIG. 5.
Figure 6B:
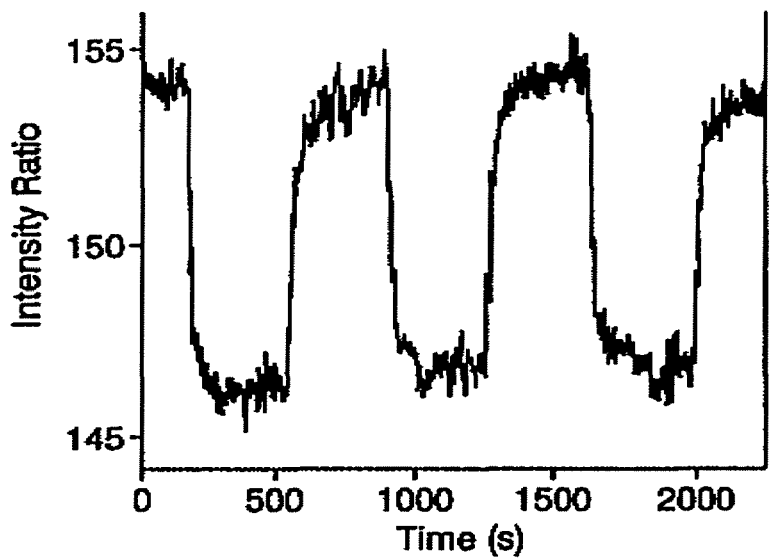

In accordance with one embodiment, the experimental set-up includes a tube connected to a bubbler placed in the proximity of the sensor and $N_2$ is purged through a solution of water: 200 proof ethanol (2:1). The vapors are periodically turned on and off in order to check the sensor's response to the stimulus. Spectra of the light emitted by the dry sensor and the wet sensor are recorded, as shown in FIG. 6a. The peak most sensitive to vapor concentrations is preferably chosen for recording the time-series of the transmitted light, as shown in FIG. 6b. (The abscissa in both graphs corresponds to the ratio of light intensity between the MSPR sensor and the flat film surrounding the sensor). The graph in FIG. 6a shows the spectral shifts in the light transmitted through a 771 nm Au-coated core due to water (the continuous line corresponding to 50% humidity at ambient atmosphere) and ethanol vapor adsorption (the dotted line corresponding to 75-80% humidity with the vapor access open). The graph in FIG. 6b shows the measured sensor response (wavelength=715 nm) to cyclic humidity changes between 50% and 80%. The arrows represent the instant when the vapor access was opened (down) or closed (up).

Figure 7A:
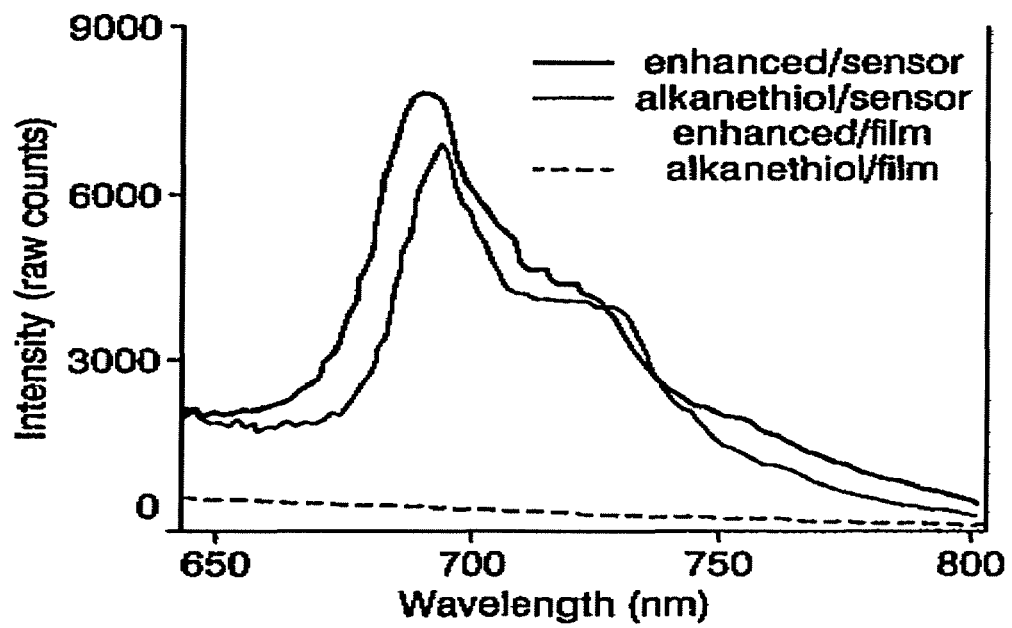
FIGS. 7a and 7b are graphs of the spectral performance and a reaction kinetics recorded by the sub-micron surface plasmon resonance sensor of the present invention under further experimental conditions.
Figure 7B:
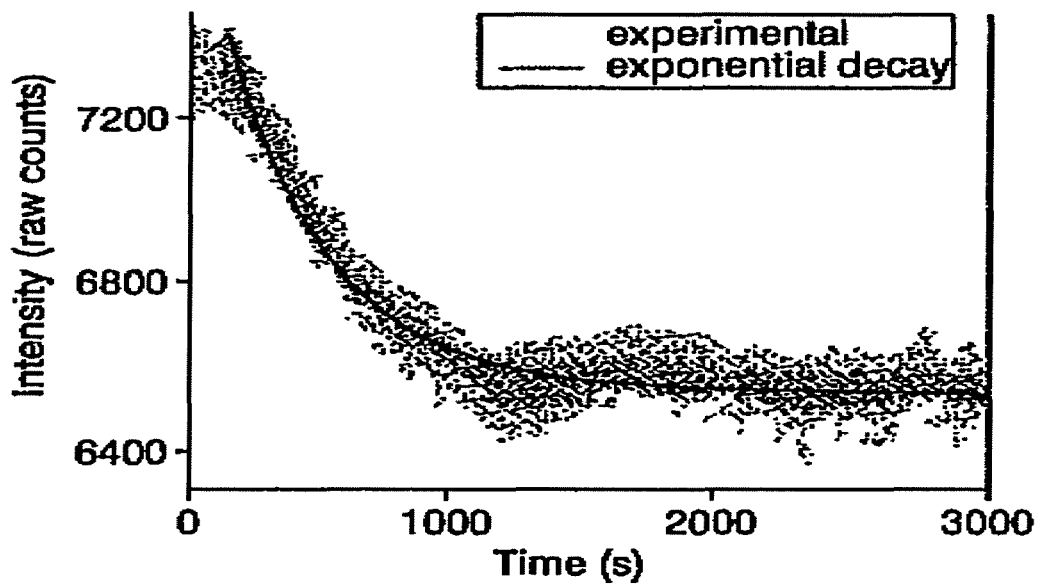

To further verify that the sensor is indeed sensitive to surface modifications, alkanethiol adsorption from ethanol may be employed as a probe. Formation of a single monolayer is known to occur in ~100 minutes at 10 mM concentrations. A comparison of the spectra is provided in FIG. 7a together with the spectral transmission of the flat gold film for the same conditions. The shift of the spectral transmission through a flat film is less than the signal that spherical cavity SPR sensor is expected to record. The spherical cavity sensor of the present invention is thus more sensitive than the flat film sensors of the prior art. The spectral shifts in FIG. 7a persist after the dodecanethiol solution is flushed with pure ethanol, indicating that irreversible adsorption of alkanethiol has occurred. The shifts are thus due to the formation of a monolayer at the gold surface. Upon measurement of adsorption kinetics and fitting with a first order exponential decay (FIG. 7b), a time constant is found for the film formation of 382±7 s at a 100 mM dodecanethiol concentration. Note that while the signal in FIG. 7b corresponds to a single monolayer about 1.5 nm thick, the signal-to-noise ratio is good enough to detect binding of fractions of a monolayer.

Example 4

Alternative MSPR Sensor Configuration

Figure 8:
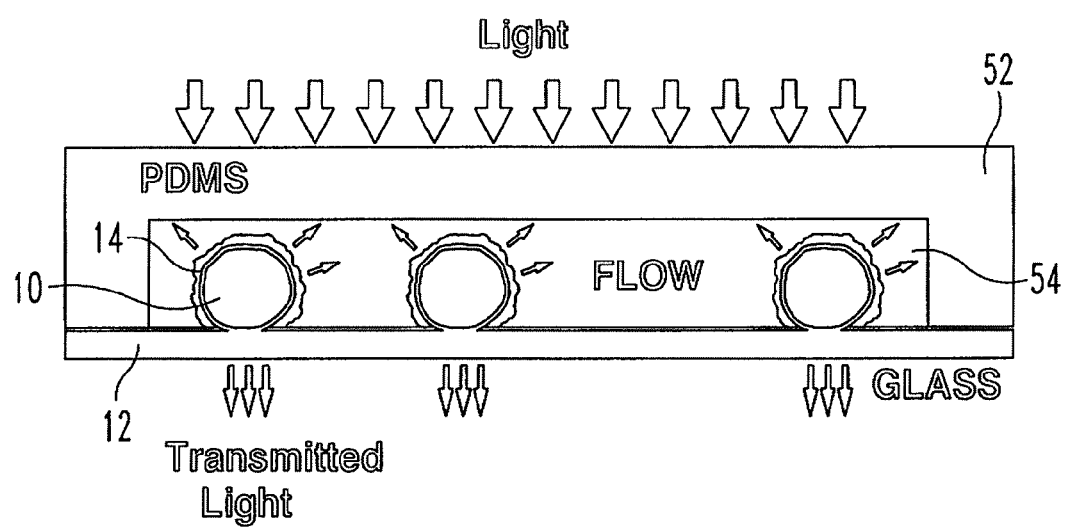
FIG. 8 is a schematic representation of a micro-fluidic sub-micron surface plasmon resonance sensor according to a further embodiment of the invention.

In Example 1 described above, the MSPR sensor responds to excitation light through the pinhole 16 (FIG. 2). In an alternative embodiment, the MSPR sensor is configured for excitation through the head, as depicted in FIG. 8. In this embodiment, cover glasses No. 1, 24 mm×50 mm and 160 µm thick are used as a substrate. NIST standard polystyrene 780±5 nm diameter nanospheres were prepared in concentrations of about $10^4$ particles/µl in methanol. (Methanol was chosen in this example because it has a very low superficial tension coefficient relative to water and therefore produces a suitable randomly mono-dispersed array of nanospheres). In the example, 70 µl of nanospheres solution was dispensed on each cover glass, providing a density of about 5,000 particles/mm². After being dried at 1 torr vacuum for an hour, the substrates were sputter coated with a 140-150 nm layer of gold in a masked region of about 10 mm long and 3 mm wide. The substrates were burnt in air plasma for about 3 minutes to ensure that the sensor was clean. Both substrates and PDMS molds were exposed for 45 seconds to air plasma prior to contact.

In this embodiment, the MSPR sensor is positioned within a micro-fluidics structure that permits fluid flow across the random array of MSPR sensors, as reflected in FIG. 8. The micro-fluidic structure may be configured as a T-shape with two micro-fluidics channels that are 50 µm wide and 20 µm deep connected to a common channel 100 µm wide and 20 µm deep. The MSPR sensors are disposed within the common channel. This micro-fluidics structure is molded into the PDMS elastomer and holes are formed in the elastomer to access the two flow channels. The flow channels are connected to two corresponding reservoirs placed at different heights. In this example, flow through the channels is thus accomplished simply by hydrostatic pressure and is on the order of 100 µm/sec. Of course, in other embodiments or commercial versions, fluid flow through the micro-fluidics structure may be accomplished in any manner, including, but not limited to, use of peristaltic pumps, syringe pumps, electrowetting and electromechanical pumps, electro-osmotic and electrophoretic pumps, micro-fluidic pumps, and the like.

In this example, a number of MSPR sensors are mounted on the floor of the common channel of the micro-fluidics device, again as shown in FIG. 8. Rather than illuminate the sensors through the pinholes (as in the previous example), the sensors are illuminated from the top through the head—i.e., through the spherical surface metal cavity. It was found that the sensor of this example exhibited a resonant response similar to that in the example depicted in FIG. 2, except that the embodiment of FIG. 8 experienced a greater signal-to-noise ratio.

One benefit of the embodiment of FIG. 8 is that enclosure of the micro-fluidics chip is facilitated. In order to enclose the micro-fluidics chips of the present invention, both the glass substrate and the PDMS mold are exposed to air plasma which modifies the chemical structure to bond the two media. Since the MSPR sensors are very small and the spacing between the nanospheres is in the range of 10-50 µm, applying the gold layer, such as by sputter coating, is problematic. In particular, it is difficult to apply the gold layer to the dielectric core particles only and not to the glass substrate. On the other hand, gold does not bond well to the glass substrate. The embodiment of the present example allows a continuous compact layer of gold to be coated onto the MSPR sensors and the glass substrate under the sensor. A layer of a material having an affinity for both glass and gold may be added to the glass substrate. In illustrative embodiments, the material may be chromium or titanium applied at a thickness of about 1-5 nm. Alternatively, the substrate may be subject to a chemical treatment to improve the adherence between the gold and the substrate. The PDMS may then be applied and flows well through the microchannels between the sensors. Post-baking the PDMS molds at 80-100° C. overnight cures the polymer and eliminates any volatiles or loose polymer chains that might contaminate the gold layer sputtered on the glass substrate.

Example 5

Functionalization of MSPR Sensors

Covalent functionalization on the gold surface of the sensor shown in FIGS. 2 and 8 allows the sensor to be covered with different target analytes, ligands or molecules, particularly biomolecules of high interest. For the purposes of the following disclosure, the term "target" or "targets" shall be used to generically refer to the target analytes, ligands or molecules that are intended to be detected by the sensor. It is understood that these "targets" may include biomolecules, such as proteins, RNA, DNA and enzymes, as well as elements other than biomolecules, such as viruses, bacteria, non-biological chemicals, and the like. However, it is understood that these "targets" have the ability to bind with other molecules provided on the MSPR sensors of the present invention and do so in a way that affects the resonant characteristics of the sensors.

Figure 9:
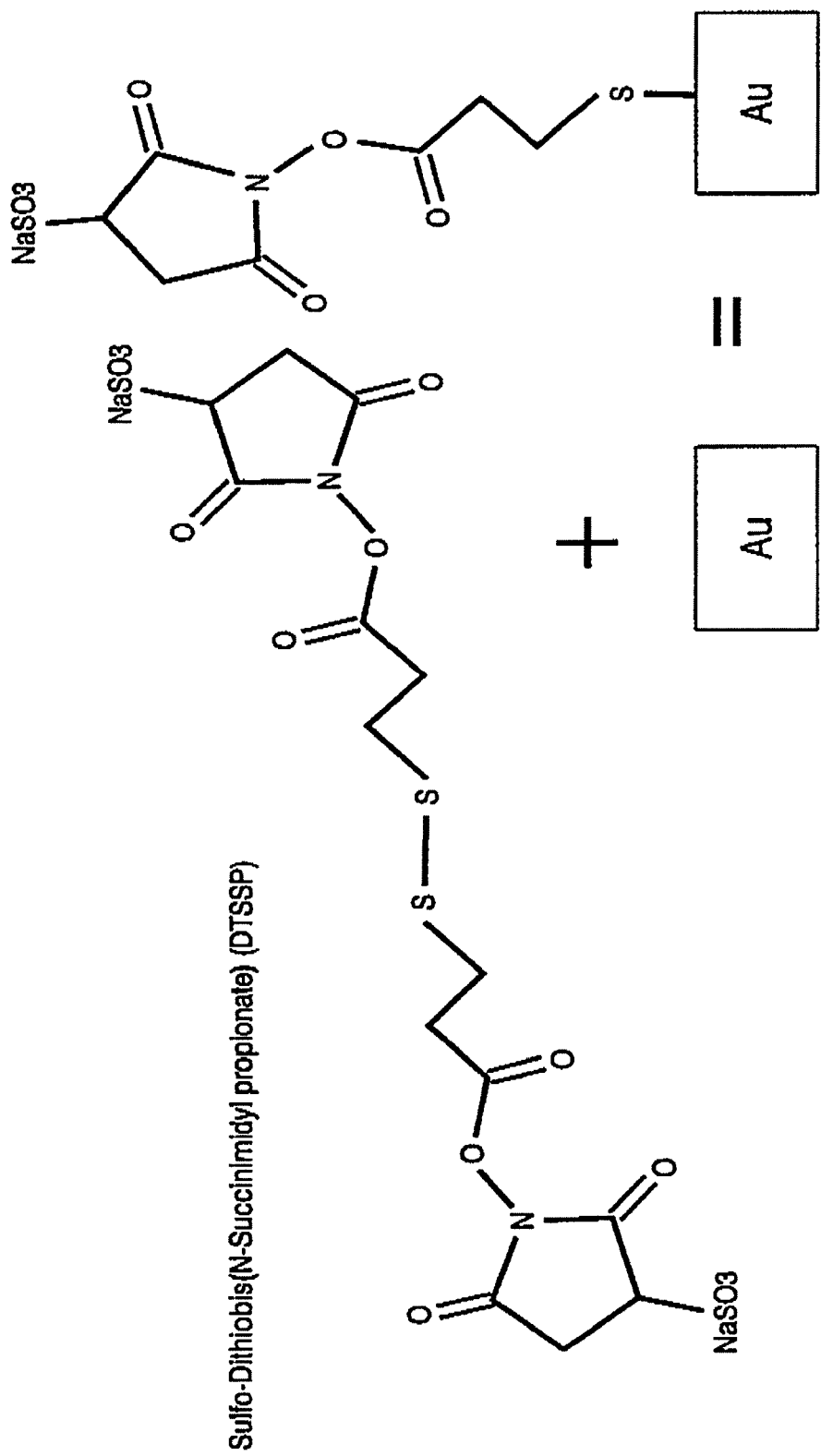
FIG. 9 is a diagram of the reaction of sulfo-DSP with the gold layer of the sub-micron surface plasmon resonance sensor of the present invention for functionalization of the sub-micron surface plasmon resonance sensor.

In accordance with certain embodiments of the invention, functionalization of the gold layer is accomplished in this example by two different chemistries in the form of a respective monolayer covalently reactive to proteins. The first chemistry is Dithiobis(N-succinimidyl propionate) (DSP, DTSP), also known as Lomant's reagent, which is a homobifunctional thiol-cleavable cross-linker that adsorbs onto gold surfaces through the disulfide group. DPS is a highly hydrophobic compound that is soluble in dimethylsulfoxide (DMSO) or dimethylformamide (DMF). A water soluble cross-linker sulfo-DPS (DTSSP) is used to avoid interaction between the DMSO or DMF and the gold surface. The functionalization reaction is illustrated in FIG. 9. In particular, the disulfide bond breaks and reacts with the gold surface.

DTSSP is a semi-stable amine-reactive NHS-ester that is protein reactive. In this example, the reaction is evaluated using two different working buffers—phosphate buffer pH 5.8 and DI water. The reaction kinetics results in a monolayer molecule of 281.52 Da and about 0.6 nm thick at a time constant of 105±8 sec. and a signal-to-noise ration of 5.5

Figure 10A:
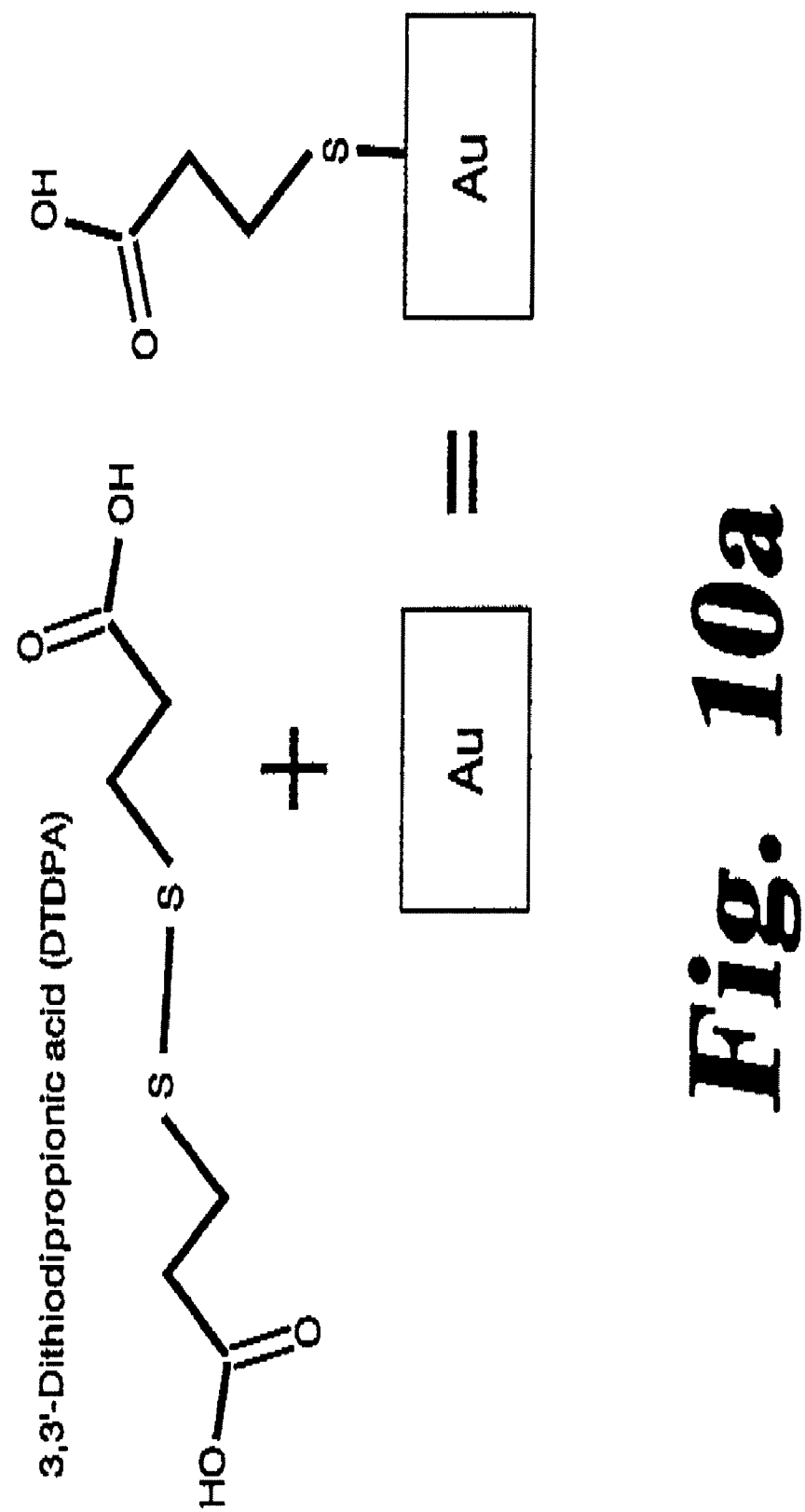
FIGS. 10a and 10b are diagrams of the functionalization reactions using Carbodiimide coupling reagents.
Figure 10B:
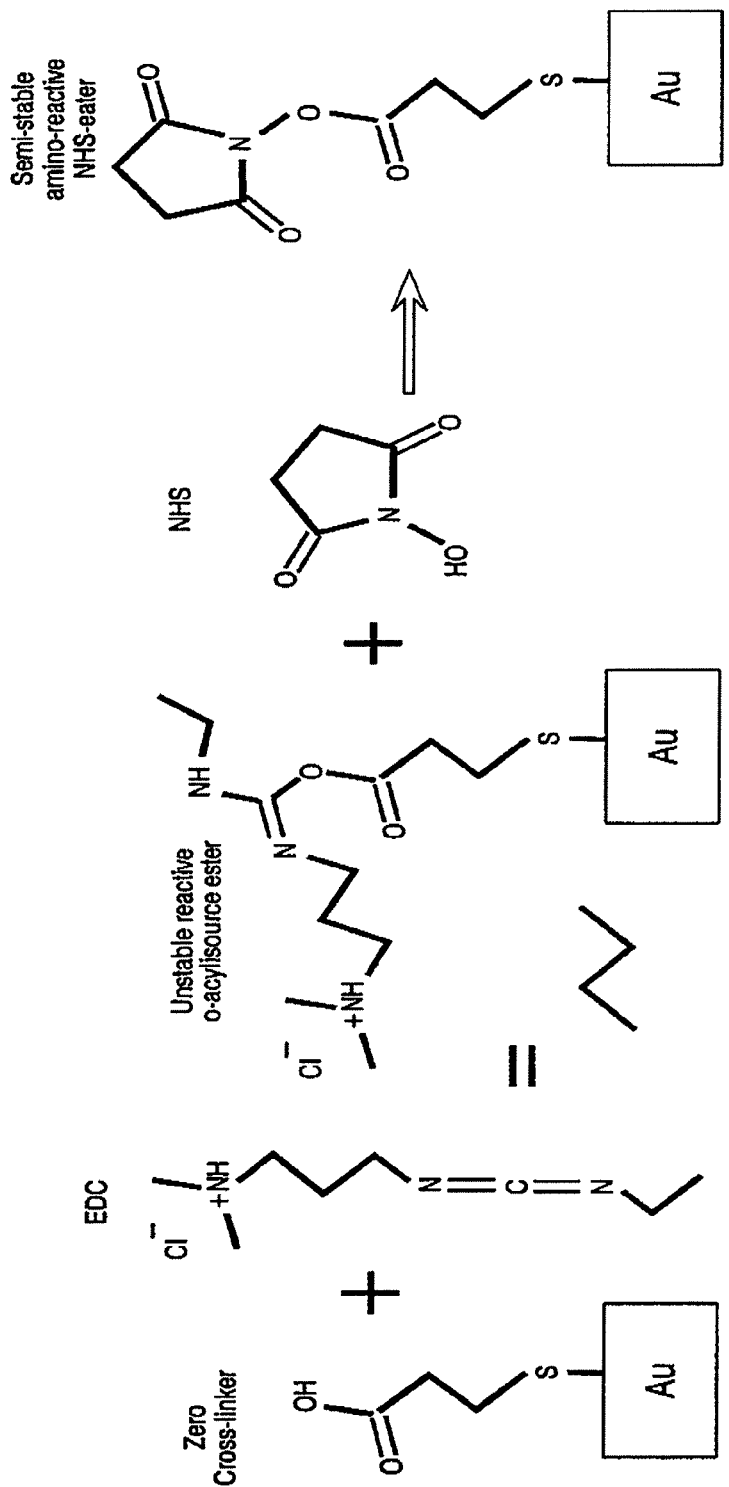

The second chemistry used for the MSPR sensor's functionalization includes Carbodiimide coupling reagents. The reaction involved with this chemistry occurs in three steps. The first step is a reaction of a zero cross-linker with the gold surface, as shown in FIG. 10a. In this first step, the cross-linker is 3,3'-Dithiodipropionic acid (DTDPA) that has a disulfide bond that easily breaks in the presence of gold. This cross-linker ends in a carboxyl group that permits carbodiimide coupling. The DTDPA reaction kinetics yields a molecule of only 104 Da and a 0.5 nm monolayer at the surface of the sensors. A carbodiimide mediator 1-Ethyl-3-(3-dimethylaminopropyl)-carbodiimide (EDC) is employed to readily react with nucleophiles. The EDC solution is prepared in ethanol because the EDC can hydrolyze very quickly. The same solution also contains an amine-reactive ester, such as N-Hydroxysuccinimide ester (NHS). In the complex reaction illustrated in FIG. 10b the EDC and NHS promote a carbodiimide coupling reaction that converts the carboxylic acid into a reactive intermediate that is susceptible to attack by amines. Thus, the final product is amine reactive and ready to bind proteins to the surface of the MSPR sensor.

The reaction kinetics of this second chemistry was found to form a monolayer of 98.1 Da and about 0.5 nm thick on top of the zero cross-linker with an estimated time constant of 28.5±0.9 sec. at a signal-to-noise ratio of 16.2.

Example 6

Protein Binding to a Functionalized MSPR Sensor

One application of the MSPR sensors of the present invention is as a bio-sensor. Uniformly gold-coated nanospheres (300-800 nm diameters) excited in white light (400-700 nm) emit characteristic wavelengths due to surface-plasmon microcavity amplification. Their emitted spectra change when molecules adsorb to the MSPR sensor surface allowing molecular interaction monitoring. In this example a monodisperse batch of nanospheres (780+/−6 nm diameter) and a constant gold thickness (120+/−20 nm) were used. Electron micrographs showed an MSPR sensor-footprint of 1.02+/−0.05 diameter (n=25). Omni-directional argon-ion sputtering should produce a sub-wavelength nanoaperture at the contact point of the nanosphere with the glass surface. The nanoapertures were measured by mechanically removing a few MSPR sensors to expose their underlying nanoapertures. Intensity profile analysis of electron micrograph images revealed a typical nanoaperture diameter of 143+/−8 nm (n=5) and showed that the gold penetrated deep under the nanospheres to form a sharp cusp. The thickness of the cusp tip was ≈1.2 nm, comparable to the gold-cluster size the sputterer produced. In one example, light is injected light through the nanoaperture into the spherical microcavity and collected the emitted light from the gold surface of the MSPR sensors. In another example light is supplied to the top of the MSPR sensors and collected through the nanoapertures from below. Surprisingly, the MSPR sensor spectra are very similar in both examples and the positions of their peaks are the same. The microcavity resonances are not present in the bare-flat-gold transmission spectrum.

The nanoapertures strongly enhance emission with respect to a flat film in both cases. Without being bound by theory it is believed that, the nanoaperture influences the formation of the microcavity resonances. When the glass is pre-coated with gold before the nanospheres are deposited, thus closing the nanoapertures, while maintaining the same total gold-layer thickness, the resonance amplitude decreased as the underlayer thickness increased and disappeared completely for underlayers of 50 nm or more in thickness. Exciting the MSPR sensors from the top produced a stronger emitted signal and was convenient for microfluidics integration. Transmission optics is simpler than the reflection optics of classical SPR.

Fixed wavelengths can be used to monitor reaction kinetics. Frequencies that showed the most sensitivity to refractive-index changes in the test medium were selected. The resonance measured at 660 nm wavelength was used to monitor reaction kinetics because it had the least overlap with neighboring peaks and because it lay in the red-NIR (near infra-red) optical window of tissue transparency, which allows use of MSPRSs to study complex media like blood, blood plasma and serum.

Because surface plasmons detect molecular adsorption to the sensor surface indiscriminately, sensor functionalization can provide molecular-interaction specificity. Typically, the sensor's surface is covered with a target-analyte-binding molecule which interacts specifically with the target analyte. A binding event increases the refractive index at the MSPRS surface, red-shifting the resonance and decreasing the emitted intensity.

Thus, a MSPR sensor functionalized in the manner described in Example 5 may be used to detect certain protein molecules that are capable of binding to the functionalized chemistries. Two important bio-molecules are glucose oxidase (Gox) and glucose (Glu).

The saturated gold-DTSSP reaction decreased the MSPR sensor-emitted intensity at 660 nm by 1,481 counts/s from 2,590 counts/s (water baseline) with a S/N=52.7 (17.2 dB). Because the cross-linker is much smaller than typical target proteins, linking the target to the cross-linker monolayer produces a dense target-molecule layer. After depositing the cross-linker, we rinsed the end of the tubing for 10 s with DI-water using a 1 mL syringe. Approximately 5 µL, of 6.25 µM GOx solution in DI-water was loaded and the DTSSP-GOx covalent binding was monitored for 1700 s as side-chain amino groups on the protein surface reacted with the cross-linker's sulfo-NHS ester group. After the MSPR sensor signal reached a stable plateau indicating reaction saturation, the sensors were rinsed with DI-water until no further change in signal was recorded. GOx binding decreased the output signal by 1,424 counts/s from 24470 counts/s (DTSSP baseline) with an S/N=50.7 (17.1 dB). The signal from the DTSSP-GOx on the MSPR sensor surface remained stable for 9 days, at which point the gold layer started to wrinkle and detach from the cover-glass. Fitting the measured data to exponentials gave reaction times of 209+/−7 s for gold-DTSSP binding and 211+/−4 s for DTSSP-GOx binding.

The same reaction kinetics for gold-DTSSP, DTSSP-GOx reactions were monitored using a Biacore 3000 with a bare-gold-surface SPR chip. The DTSSP binding produced a 643 RU signal with an S/N=107 (20.3 dB) and the GOx binding a 553 RU signal with an S/N=138 (21.4 dB). Exponential fitting yielded reaction times of 184+/−3 for the gold-DTSSP binding and 211+/−4 s for the DTSSP-GOx binding.

The MSPR sensor measured a gold-DTSSP reaction time ca. 12% longer than the Biacore, consistent with previous findings. Without being bound by theory, it is believed that this difference results from slower cross-linker adsorption on the rough sputtered-gold surface of the MSPR sensor (the gold-cluster size is comparable to the cross-linker size) than on the very smooth evaporated-and-annealed-gold film of the Biacore chip.

The MSPR sensor and Biacore 3000 measured similar GOx-reaction time constants showing that MSPRS surface roughness only affected small-molecule-gold reactions and not subsequent protein-small-molecule-gold reactions. The maximum density of GOx bound to the MSPRS surface depends on the DTSSP density which is influenced by the gold atoms' density. Crystalline gold atoms' spacing at a surface is angstrom. A DTSSP molecule has a footprint smaller than the lattice constant, so its maximum monolayer density on gold is set by the separation between gold atoms, yielding an effective area of 20.6 angstrom square/cross-linker. GOx is a dimeric protein (6 nm×5.2 nm×7.7 nm) covering an area of 37-50 $nm^2$ on a gold surface. Each polypeptide-chain subunit has 583 amino-acid residues of which 24+/−1 are at the protein surface. An average of 5+/−1 DTSSP molecules could anchor each GOx. Theoretical studies predict a maximum coverage of 55% and a GOx-mono-layer density on a gold surface of $2.7 \times 10^{10}$ molecules/$mm^2$ (4.6 pmol/$cm^2$ or 7.3 ng/$mm^2$). Experiments using scanning-tunneling microscopy, quartz-crystal microbalance and fluorescence methods find surface coverages ranging from 23% to 52%, or densities from $7.8 \times 10^9$ molecules/$mm^2$ (1.3 pmol/$cm^2$ or 2.1 ng/$mm^2$) to $2.3 \times 10^{10}$ molecules/$mm^2$ (3.8 pmol/$cm^2$ or 6.1 ng/$mm^2$). Thus, each MSPRS should bind between $1.9 \times 10^4$ and $5.7 \times 10^4$ molecules (between 32 zmol (5.2 fg) and 95 zmol (15 fg)) of GOx at its surface. The Biacore sensor similarly should bind between $10^{10}$ and $2.8 \times 10^{10}$ molecules (between 15.6 fmol (2.5 ng) and 45.6 fmol (7.3 ng)) of GOx at its surface. Despite binding $5 \times 10^5$ times as many molecules, the Biacore sensor had only twice the S/N of one MSPRS, implying that the MSPRS is ≈250 times more sensitive as determined by the number of molecules required to achieve a given S/N. In addition, the reagent flow rate for the MSPRS was only 0.5 nL/s compared to 10 µL/s for the Biacore 3000.

Because DTSSP-GOx binding might denature the GOx and binding to the sensor surface might obstruct the GOx active site, binding of the gold-surface bound GOx to its natural substrate was measured.

GOx is a FAD-dependent enzyme which catalyses the oxidation of βD-Glu to δ-gluconolactone and hydrogen peroxide. βD-Glu binds inside the active site of GOx via 12 hydrogen bonds, many hydrophobic contacts to three neighboring aromatic residues and to the FAD. Crystallography indicates that a deep pocket provides access to the FAD which is located at the bottom of the active site. α-D-glucose (αD-Glu), D-Man, 2Do-Glu and L-Glu form either fewer bonds than βD-Glu or unfavorable contacts with neighboring amino acids, decreasing their binding affinity. Hence they react slowly or not at all with GOx: αD-Glu reacts at 0.64%, D-Man at 1%, 2Do-Glu at 20% and L-Glu at 0% of the βD-Glu rate.

The two forms of D-Glu (αD-Glu and βD-Glu) interconvert and coexist in solution (prepared one day before), so a 100 mM D-Glu solution we used contains only 50 mM βD-Glu, the only isomer which binds to GOx. L-Glu served as a control for the effect of refractive index changes in the bulk substrate solutions since it does not bind to GOx but has a larger refractive index than PBS. The L-Glu solution produced rapid signal changes on wash-in and wash-out, with stable baselines for PBS and the substrate solution, indicating the absence of both specific and non-specific interactions between the L-Glu and the sensor.

The D-Glu solution produced a fast signal change due to the solution's refractive index, then slower changes due to the formation of the βD-Glu-GOx complex. The time-series for the D-Man and 2Do-Glu solutions showed identical fast changes due to their refractive indices, followed by much smaller slow changes due to their small but non-zero catalysis rates. Table 1 summarizes the reaction kinetics determined from exponential fits to the time series.

TABLE 1

Emitted-intensity changes at 660 nm from a single MSPRS during substrate interaction with a GOx-functionalized surface.

| substrates (100 mM in PBS) | L-Glu (reference) | 2Do-Glu | D-Man | D-Glu |
|---|---|---|---|---|
| $I_{baseline}$ (counts/s) | 22757 | 22725 | 22746 | 22737 |
| $I_{substrate}$ (counts/s) | 22236 | 22190 | 22168 | 21974 |
| signal ($I_{baseline} - I_{substrate}$) (counts/s) | 521 | 535 | 579 | 763 |
| noise (counts/s) | 25 | 9 | 16 | 20 |
| S/N | 21 (13.2 dB) | 57 (17.5 dB) | 36 (15.5 dB) | 37 (15.7 dB) |
| $S_{substrate} - S_{L-Glu}$ (counts/s) | 0 | 14 | 58 | 242 |
| relative rate ± error | 0.00 ± 0% | 0.06 ± 65% | 0.24 ± 28% | |

The measurements were repeated on a Biacore 3000 using an untreated-gold SPR chip. The SPR signal from the reference channel represents the difference in refractive index between substrates and PBS. We subtracted this reference signal from the equivalent signal from the GOx-functionalized channel.

The corrected SPR signal for all substrates was 25±3 RU. Their lack of variation among substrates indicated that the SPR was sensitive to the fluids' refractive indices but could not detect GOx-βD-Glu binding. It also showed that the refractive indices of the substrate solutions were indeed the same.

In another example, for one DTSSP functionalized sensor, the reaction time constant was found to be 562±35 sec with a signal to noise ratio of 3.85. This reaction covered the sensor surface with a monolayer of about 10 nm thickness. In this reaction it was determined that the MSPR sensors of the present invention exhibited a sensitivity of 42 zepto-moles/SPR sensor, or expressed as Gox mass covering the sensor a detectability of 6.7 femtograms/MSPR sensor. Variations of this procedure were implemented to monitor the Gox activity under the influence of a flow of β-D+Glucose 100 mM in PBS 1×, or a flow of Glu 1 mM in PBS 1× (to simulate normal glucose concentration in human blood), or a flow of L-Glucose, or a flow of 2-Deoxy-D-Glucose (2-DxGlu). The device in the present example was able to detect the enzymatic activity of Gox in the presence of β-D+Glucose 100 mM and 1 mM (except that for the latter case the response was much slower), but no enzymatic activity response was recorded for Gox exposed to L-Glucose or 2-DxGlu.

Example 7

Wearable Point of Care Functionalize MSPR Sensors

Figure 16:
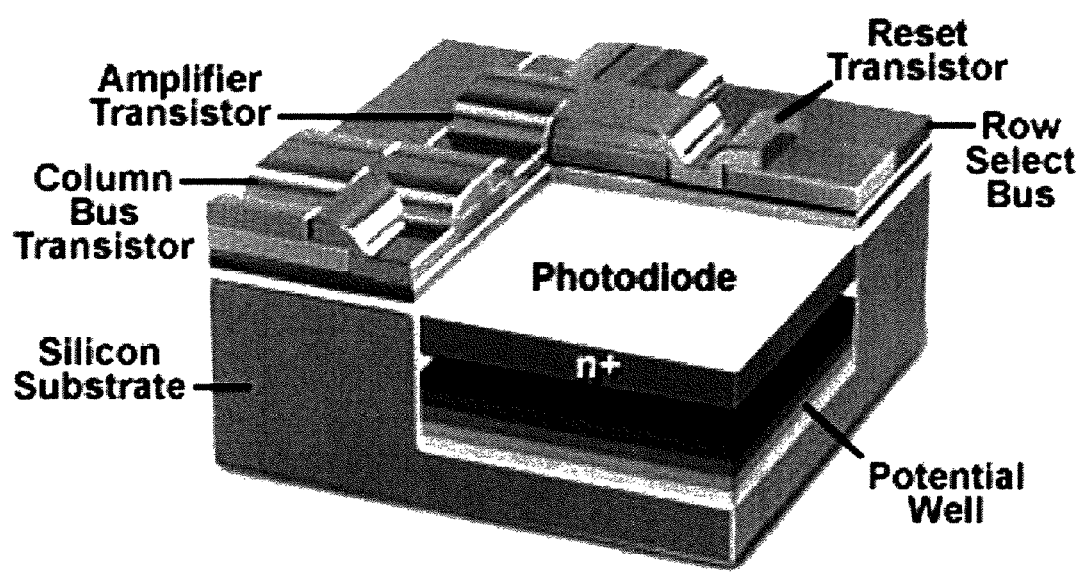
FIG. 16 shows the anatomy of an active pixel: a three-dimensional cutaway drawing of a typical pixel illustrating the photosensitive area (photodiode), metallic bus lines and semiconducting controlling transistors (adapted from the internet).

An important attribute allowing MSPR sensors to integrate into a wearable or implantable device is the size of the individual biosensors (1 micron diameter). MSPR sensors are smaller than the any detector's photo sensitive element (pixel). Pixel size in photodetectors used vary based on detector type (e.g. photodiode array, CCD, CMOS and the like.), and manufacturer, the pixel size is 5 to 10 microns (25 to 100 square microns). The majority of the pixel area, approximately 60 to 70%, is dedicated to supporting electronics incorporated into integrated circuits of the detector and controlling each pixel's photosensitive diode (e.g. metallic bus lines, semiconductor amplifiers, column buses, resets, and row select transistors) which are opaque to visible light and cannot be utilized for photon detection (FIG. 16). The photodiode area is shielded by stacked or interleaved transistors and bus lines, which are regions with increased surface roughness separating the smooth photodiode area. The remaining 30 to 40 percent represents the photosensitive diode which is only 3 to 5 microns wide and therefore 1 to 3 MSPR sensors can be randomly planted on each photodiode.

Figure 17:
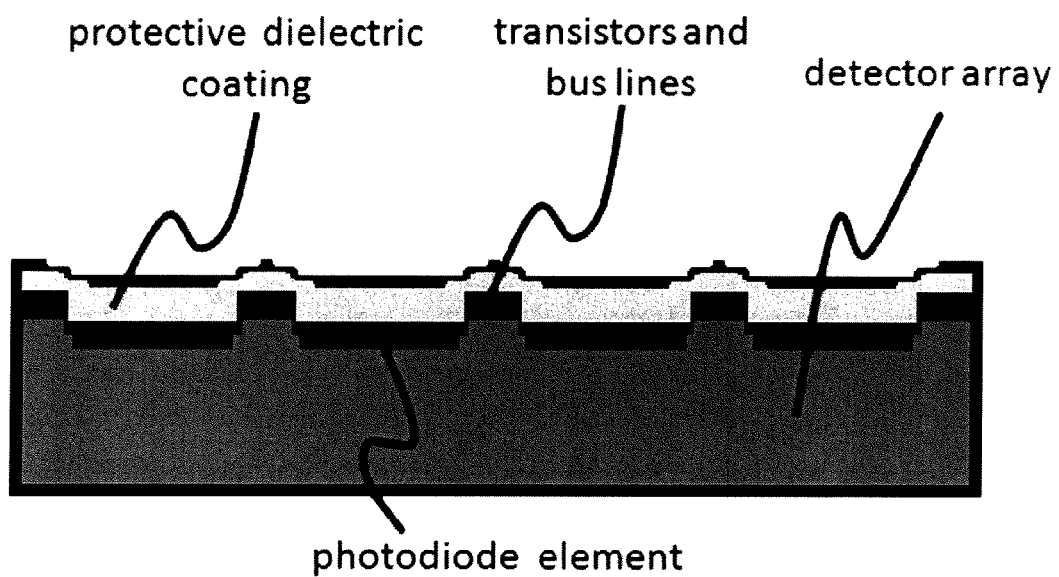
FIG. 17 shows a schematic cross-section of a detector array showing four pixels coated with a dielectric protective polymer.

These stacked and interleaved layers can lead to undesirable secondary effects such as vignetting, pixel crosstalk, light scattering, and diffraction. These artifacts are partially controlled by coating the entire semiconductor with a dielectric polysilicon, polyamide or polyimide layer (FIG. 17).

Figure 18:
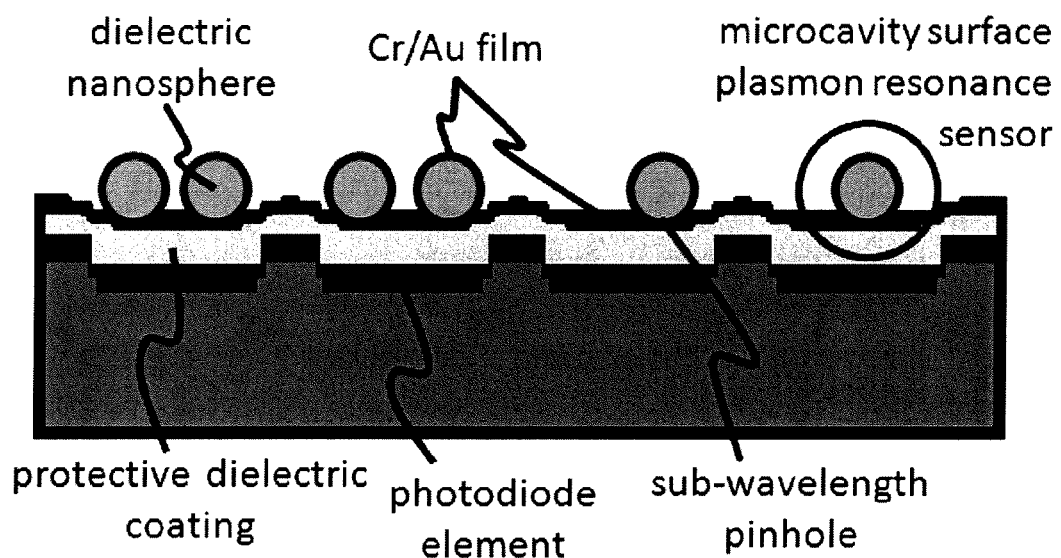
FIG. 18 shows a schematic cross-section of a four-pixel detector array showing six MSPRS manufactured directly on its photodiodes.

A protective dielectric coating as 1-1 µm (or less) thick film is applied using typical spin-coating techniques followed by polymerization of the coating according to the manufacturer's protocols. The film thickness and uniformity are measured by UV absorption. On top of the film, is dispensed 1 µl/mm² of a solution of dialectic nanospheres with a concentration $10^5$ particles/µl, generating a random distribution of from about 1 to about 4 nanospheres per pixel over the entire surface of the photodetector. The photodetector is sputter coated with a thin layer of chromium (1-10 nm) as an adhesion layer followed by a thick gold layer (100-200 nm). Omni-directional sputtering through a mask is used to form a uniform gold distribution around the nanospheres defining a sub-wavelength pinhole where the nanospheres touch the substrate. The mask allows the definition of MSPR sensor spots covering only certain pixels, thus defining regions of interest. After metal deposition, the surface of the photodetector washed removing all the nanospheres that are not covered with gold. Those regions will be used as substrate for inclosing the MSPR sensor domains with microfluidics. Pixels outside the regions of interest can be shut off and will not record any signal. The MSPR sensor and the photodiode have comparable size and the polymer coating is very thin, consequently recording of the light emitted from the MSPR sensor does not require optics between the MSPR sensor and photodiodes (FIG. 18), thus making the MSPR device size limited only by overall size of the photodetector chip. For example a ½ inch CCD with 640×480 pixels could hold up to 300,000 MSPR-pixels. The flat layer of gold around the MSPR sensor is sufficiently thick that less than $10^{-4}$ transmission of light is expected in the red-infra-red (IR) spectrum where the MSPRS resonances are excited. Light in the 640-750 nm range, which falls at the boundary between visible and IR spectrum, can also be used.

Figure 19:
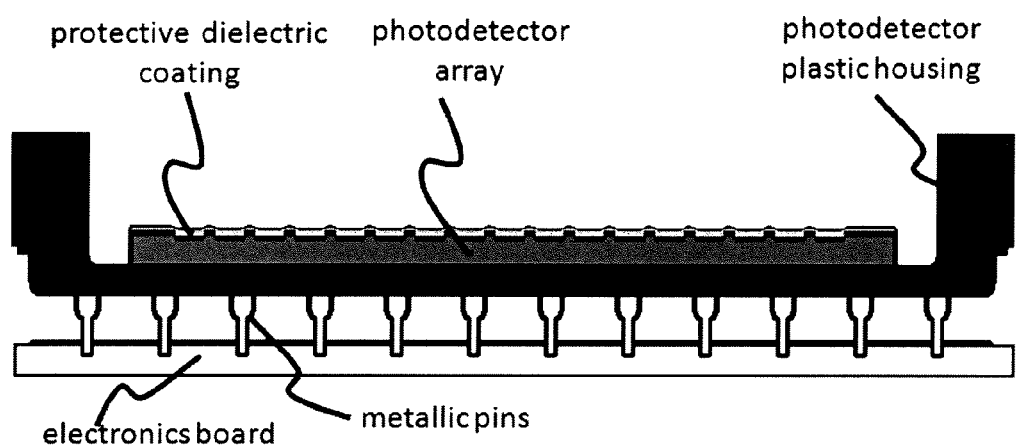
FIG. 19 shows a schematic cross-section through the housing of a photodetector chip.

Commercially available photodetector chips are manufactured within a plastic housing that includes peripheral electronics for analog signal processing, clock and timing controllers, analog-to-digital convertors, digital logic, metallic pins to connect the chip to an electronic board and like elements (FIG. 19). The photodetector housing is used as a support to integrate the MSPRS with the microfluidics that drives the analytes into contact with the MSPR sensors and to support the LED elements that are used to excite the MSPR sensor resonances.

Figure 20:
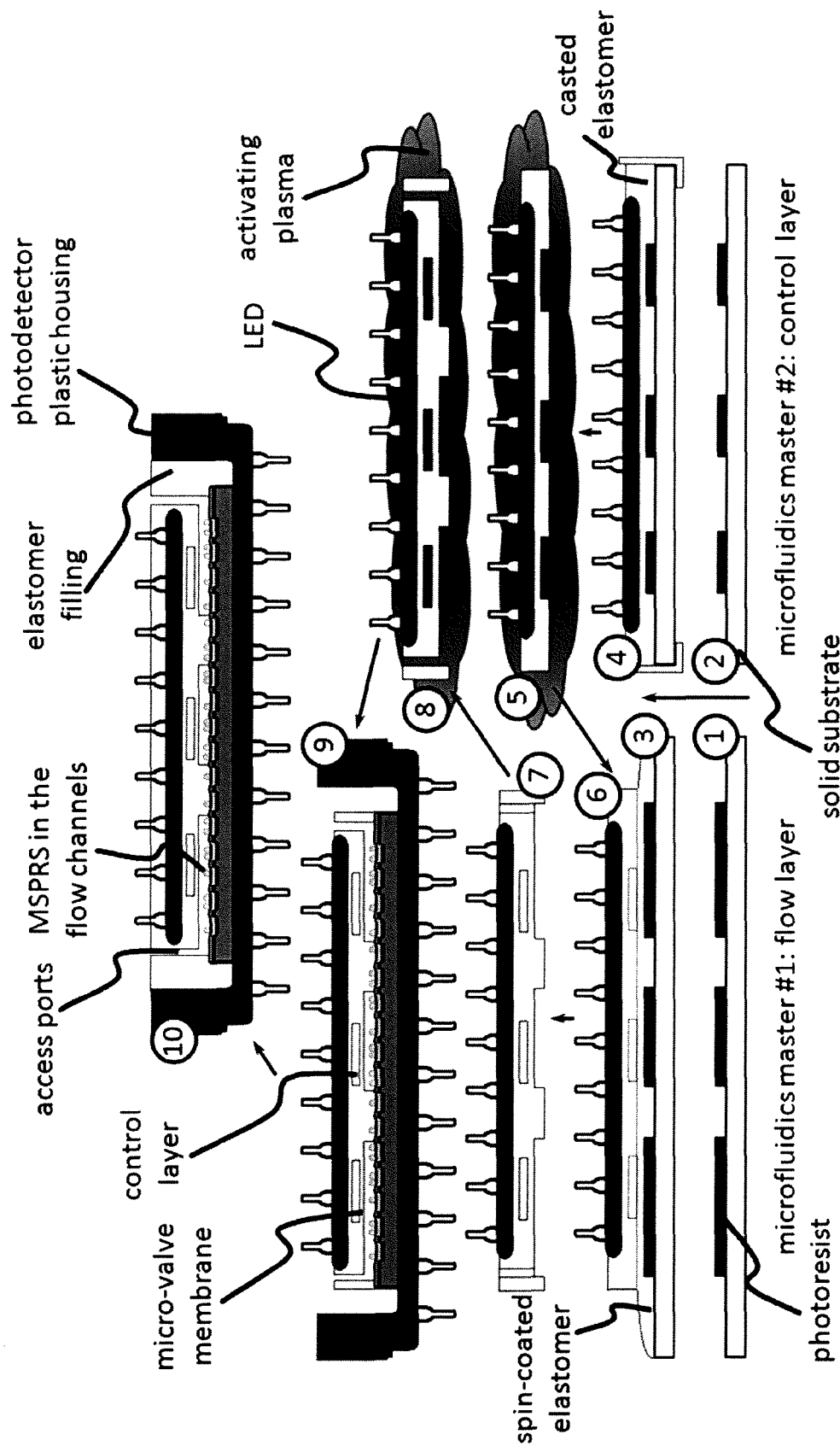
FIG. 20 shows several of the steps in integration of sub-micron surface plasmon resonance sensors, LEDs, and photodetector arrays with microfluidics.

The desired channel network and its adjacent microfluidics elements (microvalves, micro-pumps, mixers, pre-concentration modules, microfiltering modules, and the like.) are designed using common practice in microfluidics (see steps (1) and (2) in FIG. 20). The replica of these elements is cast into stamps (masters) using common photo-resistant polymers (e.g. SU-8, PMMA, SPR-220, and the like.) on hard substrates (e.g. glass slides, silicon wafers, plastic, fiber glass substrates, and the like). The first microfluidic master is a replica of the flow channels that bring the analytes in contact with the MSPR sensor, the mixer, pre-concentration and filtering microfluidics modules that process the blood sample before reaching the MSPR sensor. The second microfluidics master is a replica of the control channels, including microfluidics valves and pumps. In step (3) elastic polymers (e.g. poly-dimethylsiloxane, PDMS) are poured on master #1 and spin-coated until 20 to 50 µm thick layers of elastomer are obtained. The obtained coatings are polymerized it according to manufacturer protocols and left on the master until step (6) in FIG. 20 to avoid the possible difficulties of removing such a thin layer of elastomer. In step (4) the master #2 is surrounded with a solid barrier and an elastomer is poured onto the master #2 until 3 to 5 mm thick layers are obtained. The LED array is dipped it in the elastomer while aligning it with respect to the MSPRS spots. The assembly is kept under vacuum for 1 hr to remove any air bubbles formed during the pouring step, followed by polymerizing the elastomer according to manufacturer protocols. The LED remains inside the elastomer. In step (5), the mold of the control layer from master #2 is peeled off and cut at the right dimensions eliminating edge artifacts induced by the casting barrier. Access holes (i.e. access ports) are cut which connect the control channels with outside tubing. The molds are then plasma-cleaned for 30 sec to activate the outside surfaces. In step (6), after activation (plasma-cleaned), the control layer and the flow layer, which is still on the master #1, are carefully aligned brought into physical contact. The activated layer forms an irreversible bond with the flow layer. In step (7) both layers are peeled off and cut at the appropriate dimensions. The assembly is perforated to provide a new set of access holes (i.e. access ports) which connect the flow channels with outside tubing. In step (8) the bottom surface of the new mold is activate using an air-plasma. In step (9) the microfluidics ensemble is brought into physical contact with the protective dielectric coating of the photodetector forming a tight seal. In step (10) the remaining space of the photodetector housing is filled with a polymer precursor and kept under vacuum for 1 hr to eliminate unwanted air bubbles. The polymer precursor is polymerized according to standard protocols. This results in a compact microfluidics chip that contains a tight sandwich-like structure with photodetector diodes under the MSPR sensor(s) (i.e. on the side nearest the pinhole(s) defined at the interface between the MSPR sensor(s) and the substrate) and LED on top (i.e. the side away from the pinhole(s) defined at the interface between the MSPR sensor(s) and the substrate. It is appreciated that the MSPR sensors can be constructed such that the pinhole defined at the interface between the MSPR sensor(s) and the substrate is nearest the LED layer, by modifying the process to construct the MSPR sensors on the LED layer. Access ports permit connection of this chip's microfluidics to outside controllers. The physical dimensions of this chip are defined by the photodetector size (see step (10) in FIG. 20).

In one illustrative example, monitoring of analytes (e.g. blood makers) is realized by tracking changes in the time constant and the saturation level of the interaction of the analytes with specific ligands fixed on the surface of the MSPR sensors. Both parameters vary with analyte concentration. The kinetic constants (rate of association, $k_{on}$; rate of dissociation, $k_{off}$; or equilibrium binding constant, $K_a$), are either known or can be determined easily. Collection of a data set, which represents the interactions of one analyte with its specific ligand, may take 15-25 min depending on the interaction characteristics. Data points are collected every 1-10 sec, defining a characteristic interaction profile which is dependent on the analyte concentration.

A possible disadvantage of continuously monitoring the concentration of chemical markers (analytes) in blood is that after the interaction between the marker and ligand reaches a saturation level (FIG. 21) the detection becomes less sensitive to marker concentrations. Therefore the sensing surface requires regeneration, i.e. a step in which the analyte is washed off the sensing surface until the signal returns to the near the initial baseline value. During this step there is no monitoring of the analyte level by the regenerating MSPRS leaving the patient unattended. These non-monitored periods can be avoided by utilizing a microfluidic network which includes two sequential cycles thereby eliminating dead times between data sets, continuously monitoring the patient's blood markers.

A microfluidic network capable of continuously monitoring six sepsis blood markers: interleukin-1 (IL-1), interleukin-6 (IL-6), interleukin-10 (IL-10), interleukin-13 (IL-13), transforming growth factor-β (TGF-β), and tumor necrosis factor-α (TNF-α) (see FIG. 22) may be used for detection and/or monitoring sepsis.

Figure 22:
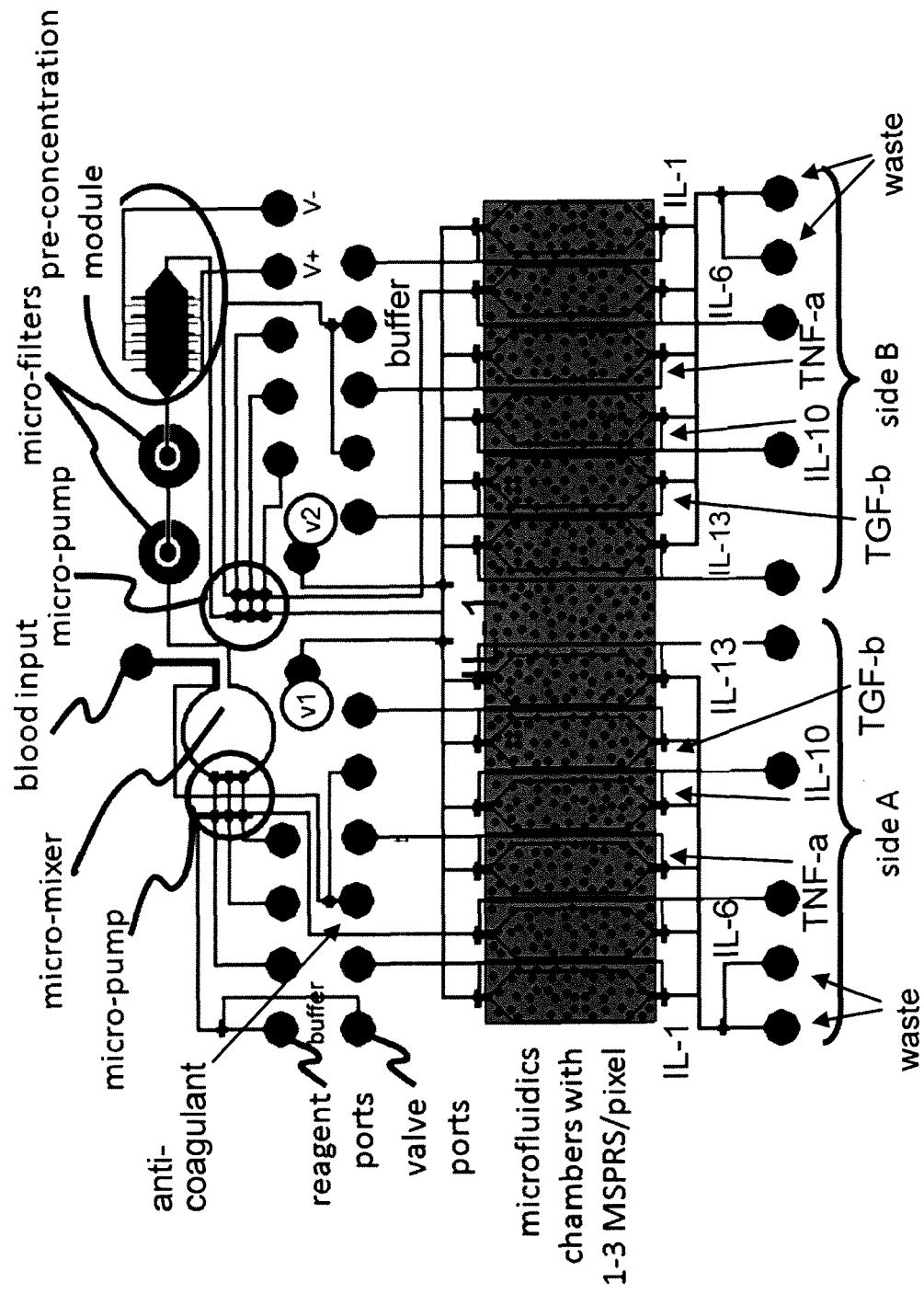
FIG. 22 shows an illustrative multifunctional microfluidic network consisting of two sets of 6-microfluidic chambers each used to test for a sepsis blood marker. The two sets work in parallel: while side A is monitoring blood levels of a blood marker, illustratively IL1, IL6, TNF-α, IL10, TGF-β, IL13, or the like, side B is being washed and prepared for a new set of reactions. After side B is washed the roles of side A and B are reversed.
Figure 23:
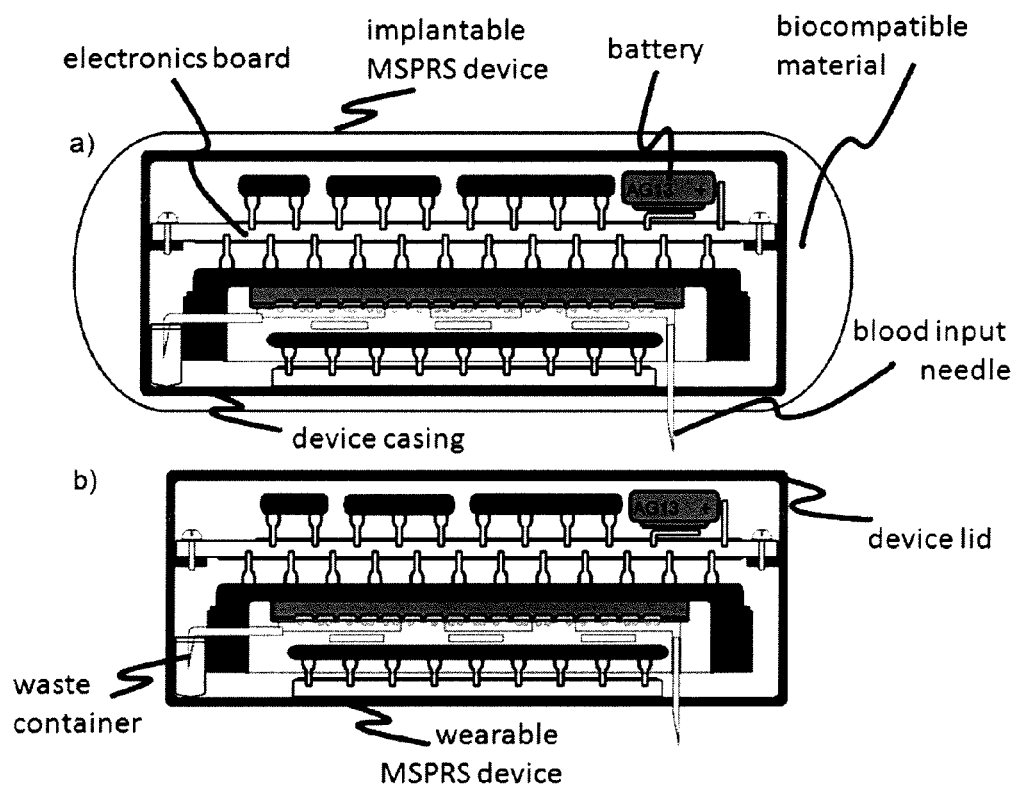
FIG. 23 shows schematic cross sections though a sub-micron surface plasmon resonance sensors implantable device (a) and a sub-micron surface plasmon resonance sensors wearable device (b). (a) The implantable device is encapsulated in a biocompatible material that can prevent adverse interactions with surrounding live tissue. (b) The wearable device is attached to the body by an adhesive pad or patch, or a wrist, arm, leg, chest or waist band (FIG. 24).
Figure 24:
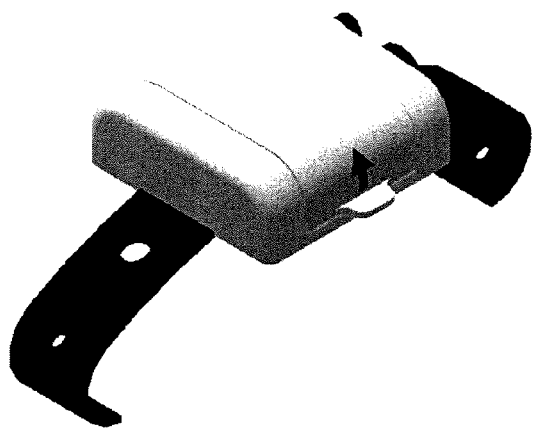
FIG. 24 shows an illustrative example of a wearable MSPRS device showing casing (see cross section in FIG. 23 panel b) and wristband.

The network has two sides (A and B, FIG. 22) each side has six chambers functionalized to detect one of these analytes (blood markers). Each chamber covers about ~20 pixels (FIG. 22), or 20-40 MSPR sensors. The microfluidic network has a blood line input directly connecting to the patient blood vessel by a needle which is part of the device's case (FIG. 23). A micro-mixer actuated by a downstream micro-pump mixes the fresh blood with anti-coagulants (e.g. heparin, argatroban, lepirudin, bivalirudin, hementin, batroxobin, and the like.) or calcium chelators (e.g. EDTA, oxalate, citrates, and the like.) to prevent blood coagulation before entering the chip. Two micro-filters with selected porosities and large capacity will remove the blood particles (e.g. erythrocytes, leucocytes, thrombocytes, and the like) which represent about 45% of the whole blood. The capacity of these micro-filters is chosen to correspond with the volume of blood likely to be processed during length of time the patient is under observation. The blood extract (blood plasma) is than driven into a pre-concentration module to increase the concentration of proteins that pass through the filters, thus increasing the signal generated by the analytes interaction with the MSPR sensors improving detection of the analytes (blood markers). A second micro-pump is used to pull the plasma through the filters and pre-concentration module and push the filtered, concentrated plasma towards the detection chambers. Valve (v1) and (v2) sequentially direct the input blood plasma towards side A or side B of the chip automatically (FIG. 22).

After the chip is manufactured, the MSPRS are functionalized with antibodies directed against the analytes (blood markers) of interest. The sensitivities of the MSPRS to the analytes of interest are determined. The functionalized chip is then marked with a bar code encoding for the functionalization reagents (or analytes of interest) and calibration test information. The tested chip ((10) from FIG. 20) is then integrated into the wearable or implantable device (FIG. 23) where it is connected to the electronics board, blood input needle or micro needle, input buffer container(s), and waste container(s).

Before the implantable or wearable device is connected to the patient's blood stream, the device will run a calibration cycle to establish the baselines for the two chambers (FIG. 6). The device is connected to the patient blood stream and monitoring started. In this illustrative example the selection of blood marker allows 20-min monitoring cycles. After a baseline run, $t_1$=10 min, valve (v1) is turned on and valve (v2) turned off (FIG. 22) to direct the blood towards one chamber. While side B continues to run buffer, side A is running blood plasma and the signal shows an exponential decay, away from the base line, indicating the interaction of the blood marker with a specific ligand fixed at the sensing surface. After 10 min ($t_2$=20 min), the reaction reaches a saturation plateau which is monitored for an additional 10 min before switching the valve (v1) off and the valve (v2) on at $t_3$=30 min. Now, side A is washed with buffer, which can be a mild elution solution (e.g. buffer, buffer with a modified pH or ionic strength, or a different buffer, or the like), and side B is exposed to blood plasma. The signal from Side A slowly returns to value of about the initial baseline value and the signal generated by side B shows an exponential decay characteristic of the interaction. After cycling through the side A and side B a number of times determined by the level of the analyte of interest, the device is capable of calculating ("learning") a normal analyte (i.e. blood marker) level range (dashed line, FIG. 21) characteristic to that patient. By automatically fitting the exponential decay curves, the time constants ☐ ($k_{on}$, $k_{off}$, C) can be recorded. Any portion or all of this data can be stored and used by software supplied with the device to determine if and/or when the patient may be entering into a state of septic shock. It is appreciated that fluctuations for the measured variables will occur; consequently, it may be advantageous to connect the patient to the instrument as soon possible so the instrument can learn the patient's blood marker levels and the intrinsic or normal range of fluctuations in the blood marker levels for that patient.

Figure 21:
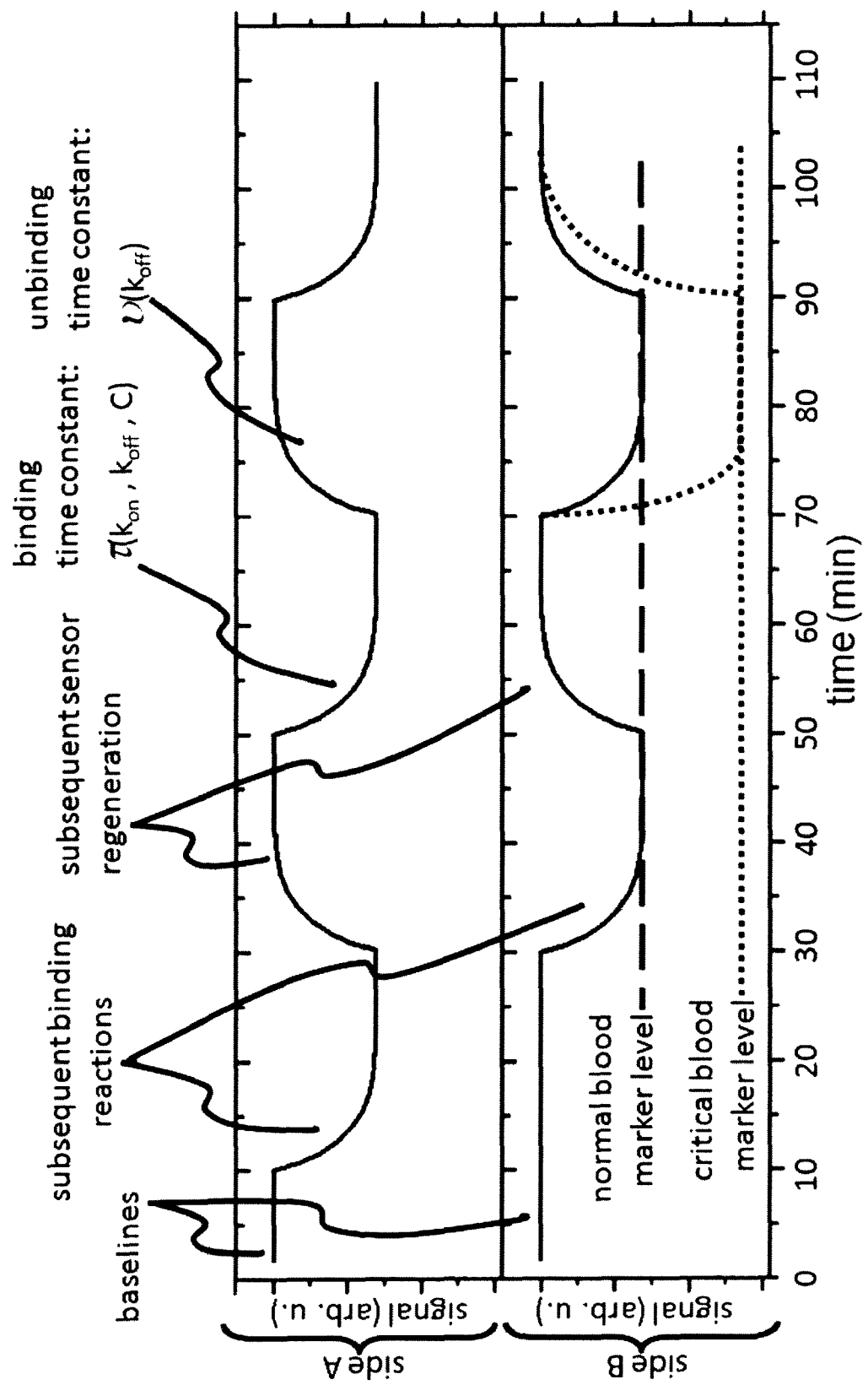
FIG. 21 shows an illustrative sub-micron surface plasmon resonance sensors emitted signal recorded by a wearable or implantable device.

In FIG. 21 is shown a case where after about an hour of monitoring ($t_4$=70 min), the patient has an increase in his/her blood marker level due to an infection which might later cause the patient to enter into septic shock. The new recorded signal is characterized by a different interaction time constant. An increased concentration often results in a smaller value for the time constant leading to the saturation plateau being reached sooner and further away from the baseline than for normal concentrations of the blood marker (dotted line, FIG. 21). When this deviation from normality is recorded, the instrument can alert medical personnel. It will take about 5 min (more generally, a time near the average for the time constants which are characteristic for the interaction of the analyte with the MSPR sensor) for the instrument to react to such a change in the blood marker level. The deviation from a normal value for the blood marker is likely to continue until the patient is administered proper care, after which the blood marker concentration will decrease to its normal levels.

There are two factors that are important in determining the size of each implantable or wearable device. One of those factors is the size of the photosensitive chip and the second is the size of the containers required for waste, anticoagulant and buffer solution. There is a tradeoff between the size of the chip and usable life of a particular device. For the wearable devices the size is not as limiting as for an implantable device. For an implantable device it is advantageous for the device to be as small as possible. Flows of 1-10 nl/s are common in microfluidic practice which for a 24-hr continuous use translates into about 0.1-1 ml of analyzed blood. It is contemplated that an equal volume for the elution buffer and another 10% for the anticoagulant can be used. Consideration of several factors suggests that implantable devices with a footprint of about 2×2×0.5 cm are achievable. Larger wearable devices, about wrist watch size, can be customized to continuously work for up to a week.

The MSPR sensor implantable or wearable devices require electronics and software to control the photodetector chip, LED, microfluidic valve, micro-pumps, pre-concentration module, to store and analyze the data and communicate with the doctor office. It is also contemplated that the devices described herein can include wireless communication capability. Information about the levels of analytes measured by the device can be wirelessly communicated to another device, e.g. a handheld, notebook, notepad, or desktop computer, a nearby data station, a data relay station, and the like) which can contain additional electronics and software for analyzing the signal and providing reports and/or alarm signals.

The above examples demonstrate the efficacy of the MSPR sensor and micro-fluidics features of the present invention in detecting large and small targets, including bio-molecules such as important proteins. In particular, the MSPR sensors of the present invention can be configured to a footprint of less than 1 μm and are still capable of detecting specific binding of zeptomoles of unlabeled targets. In accordance with the present invention, the light source in the optic setup may be a laser diode. In several examples, the selected laser diodes resonated at a wavelength of 590 nm; however, it is contemplated that other small laser diodes may be used at other wavelengths. It is believed that a laser diode resonance at a wavelength of 632.8 nm may help optimize performance of the SPR sensors of the present invention.

It is contemplated that light sources other than the above-described laser diode may be used. For instance, in certain alternative embodiments, a light source may incorporate an optical filter operable to limit the transmitted light to a desired wavelength(s). The optical filter may be tuned at the time of installation of the MSPR sensor to a specific resonant frequency. Alternatively, the optical filter may be positioned at the detector side of the sensor.

The selection of optical detectors can enhance functionality and efficiency of the MSPR sensors of the present invention. In one specific embodiment, the detector may be a low dark current silicon avalanche photodiode (APD) photon counting detectors. Alternatively, for detecting multiple targets in parallel, a CCD chip or other pixel oriented device may be used. The detectors and associated electronics can determine a baseline resonant peak for the MSPR sensors to calibrate the sensor. In use, the detectors may determine whether the resonant peak has shifted (red or blue), which is a direct indication that the target has bound to or left the resonant surface of the MSPR sensor.

The invention contemplates detectors that are qualitative—i.e., that simply detect the presence of a particular target—or quantitative—i.e., that detect concentration or change in concentration of the target. In the latter case, a quantitative analysis can be particularly valuable to measure the change in analyte concentration over time. For instance, changes in certain toxins in a patient's blood may be monitored, rather than simply discrete instantaneous level, thereby facilitating early diagnosis of a harmful medical condition. The example herein regarding detection of sepsis may benefit from this quantitative approach. Similarly, at home quantitative monitoring of blood sugar levels may be used for earlier detection of diabetic conditions.

In the embodiments described above, the gold layer is sputter coated onto the dielectric nanospheres planted on a glass substrate. Adhesion between gold and glass is poor, therefore the manufacturing process may include sputtering a thin layer of chromium onto the glass before adding the gold layer, since chromium binds well to glass and gold binds well to chromium, For high throughput manufacturing, both layers may be applied by a twin target sputter coater to avoid the need to break the vacuum around the substrate.

Figure 11:
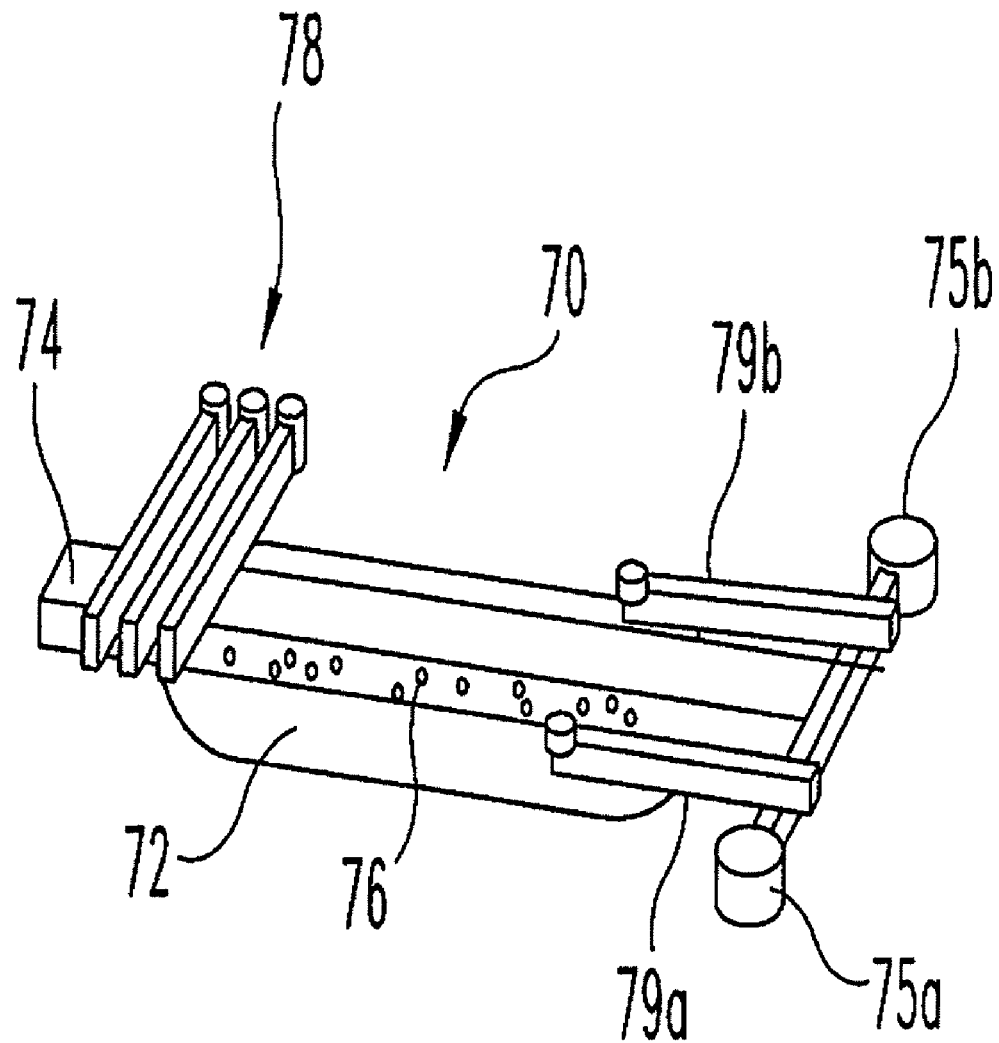
FIG. 11 is a diagram of micro-fluidic components mounted on a micro-fluidic sub-micron surface plasmon resonance sensor of the present invention.

In the above examples, fluid flow through the micro-fluidics device was accomplished by hydrostatic pressure only. Alternatively, the micro-fluidics sensor chip may incorporate micro-valves and micro-peristaltic pumps to control fluid flow and sample delivery. The use of this micro-fluidics technology will also allow the MSPR sensors of the present invention to process small sample volumes, on the order of 1 μl range. Thus, a micro-fluidics MSPR sensor device in one embodiment of the invention may be configured as shown in FIG. 11. The device 70 includes a MSPR sensors as the domain 72 with a T-shaped micro-fluidics structure 74 mounted thereon. The T-shaped structure 74 operates in the manner described above to direct fluid from the channels 75a, 75b of the structure to the common channel 76 over the MSPR sensors. A second layer of the micro-fluidics MSPR sensor device 70 includes micro-valves and micro-pumps as fluid control components. In particular, a micro-fluidic pump 78 is provided at the discharge end of the common channel 76. In various embodiments, the micro-pump may be peristaltic, thermal, piezo-actuated or the like. Each channel 75a, 75b is provided with a corresponding micro-valve 79a, 79b to control fluid flow through the respective channel into the common channel 76. In a single analyte detection sensor, such as the micro-sensor 70 shown in FIG. 11, one channel 75a and valve 79a controls flow of the sample into the common channel, while the other channel 75b and valve 79b controls flow of the functionalization solution.

It is contemplated that the micro-fluidics components may be electronically controlled to operate in a pre-determined sequence for functionalizing the MSPR sensor array and analyzing a fluid sample. In particular, valve 79a may be closed and valve 79b opened to permit introduction through channel 75b of functionalization solutions, such as the functionalization composition as described above. Once the MSPR sensors are functionalized, a buffering solution may be introduced through the channel 75b. The valve 79b may then be closed and valve 79*a* opened to accept the sample fluid through channel 75*a* to contact the fully functionalized SPR sensor array. Of course, it is contemplated that the functionalization step may occur remote from the sample analysis—i.e., in the preparation of a pre-packaged biological micro-sensor.

In addition, the micro-pump and micro-valves may be controlled as necessary to ensure sufficient formation of the monolayer of the target on the functionalized MSPR sensor. For instance, in the Gox example above, the formation of a 160,000 Da monolayer about 10 nm thick was detected with a time constant of about 562 seconds. Thus, the flow of test fluid through the micro-fluidics chamber must be adequate to ensure the formation of a significant and detectable monolayer of the target.

Another aspect of the fluidics element of the inventive sensors is dependent upon the nature of the fluid sample being evaluated. In particular, a complex sample requires pre-cleaning and pre-concentration before analysis to ensure accurate detection results. Such complex samples include human blood, which may be evaluated for certain proteins as described in the functionalization examples above, and natural water, such as water from a river being evaluated for the presence of dangerous pathogens. Pre-cleaning and pre-concentrating a biological sample may occur prior to introduction into the MSPR sensor system. For instance, centrifugation may be used to clean a fluid sample, but centrifuge machines are not adapted for a micro-fluidics environment. Large-scale sample testing, such as a drinking water purity monitor, may be amenable to this scale of pre-cleaning and pre-concentrating. However, one feature of the present invention is that is very well suited for micro-fluidics applications in which the entire sensor and associated sample fluidics are present on a single small chip.

Figure 12:
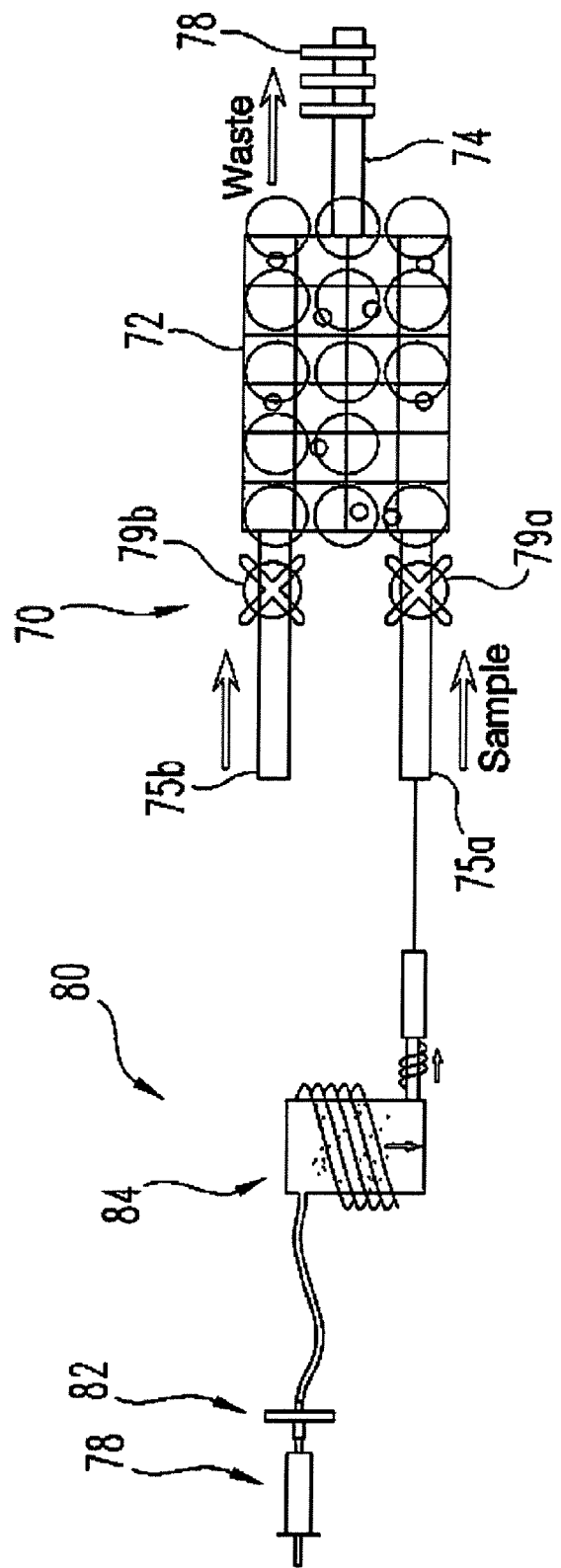
FIG. 12 is a diagram of a micro-fluidic sub-micron surface plasmon resonance sensor of the present invention with micro-fluidic pre-filtering and pre-concentration modules.

Thus, the present invention contemplates the addition of micro-fluidic filtration and pre-concentration modules that are integrated onto the MSPR sensor chip. Thus, a system 80 shown in FIG. 12 may incorporate a micro-fluidic filter module 82 and a pre-concentration module 84 upstream of the MSPR sensor chip, such as the chip 70 illustrated in FIG. 11. In this embodiment, the upstream modules are connected to the fluid sample channel 75*a* and valve 79*a*. Similarly, FIG. 22 shows micro-fluidic filters, micro-pumps, micro-mixers and pre-concentration modules being integrated into a microfluidic MSPR sensor device.

The micro-fluidic filter 82 in a specific embodiment includes a porous membrane sandwiched between opposing PDMS molds. The flow area of the filter depends upon the fluid sample being tested. For instance, a filter area of about 2.5 cm² is sufficient for low volume filtering, such as up to 1 ml of blood which could allow operation of a chip for up to 24 hrs. Larger filter areas may be used for higher volume, or higher flow rate sampling, or longer periods of operation.

In general, filtration removes some of the targets that are desired to be detected. For instance, many proteins will non-specifically bind to filter membranes. Thus, in some cases a pre-concentration module 84 may be interposed between the filter module 82 and the sample channel 75*a* of the microfluidics sensor chip. A variety of pre-concentration approaches may be acceptable, such as electrophoresis, capillary separation, functionalized magnetic nanoparticles, isotachophoresis, column separation or photo-activated polycarbonate (PPC) micro-fluidics chips.

Figure 13:
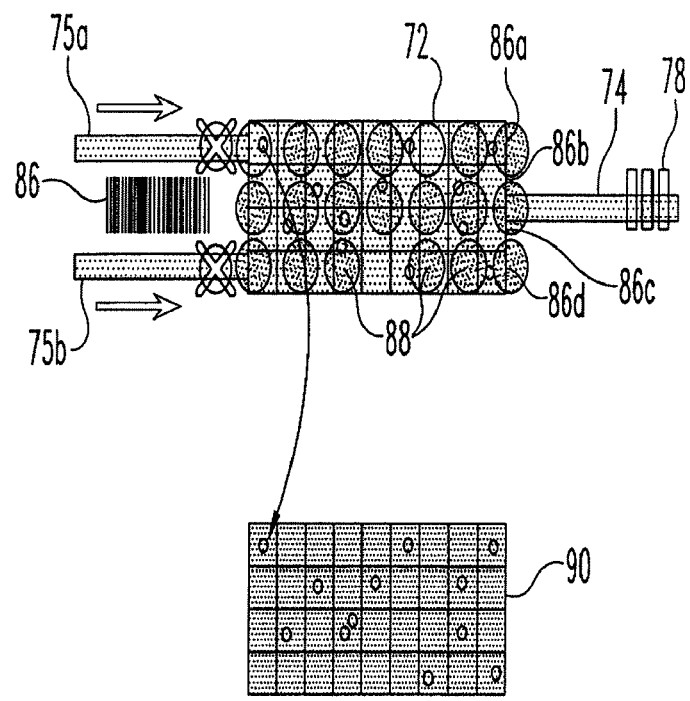
FIG. 13 is a diagram of a micro-fluidic sub-micron surface plasmon resonance sensor of the present invention with mapped functionalization for detecting multiple molecules, ligands or analytes.

The small size and the accuracy of the MSPR sensor chip of the present invention allows the fabrication of sensors with throughput and massively parallel processing capabilities, up to 10,000 MSPR sensors per mm², that greatly exceed the capabilities of current sensors and biosensors. In particular, the MSPR sensors of the present invention can be configured to detect thousands and even millions of targets, all on a single small sensor chip. As shown in FIG. 13 the sensor chip includes a plurality of MSPR sensors on a single chip that may be arranged in randomly mono-dispersed arrays or in periodic arrays. The arrays of MSPR sensors may be produced using photolithography, droplet-based microfluidics and/or holographic optical tweezing, or any other suitable technique for placing microscopically small objects onto a glass substrate. However, one feature of the present invention is that millions of the micro-sized MSPR sensors may be completely randomly dispersed on the substrate using currently available technology. As explained below, in spite of this random dispersion of MSPR sensors made according to this embodiment of the invention, they may be fully functionalized to detect a vast number of targets.

In order to accommodate the need to detect multiple target, current planar SPR sensor technology requires uniformly distributed SPR elements to ensure adequate detection capabilities for multiple targets. The relatively low sensitivity of these current sensors dictates that a sufficient number of SPR domains be associated with predetermined "spots" in which all elements are functionalized to a particular target. However, the ability to accurately place uniformly distributed SPR elements is very limited, generally not exceeding a 50 by 50 grid of elements. This limitation, coupled with the accuracy limitations of the current planar sensors, ultimately limits the number of discrete targets that can be detected to less than about 1,000, which ultimately severely limits the range of applications for these sensors. For instance, gene therapy and human genome mapping projects yield millions of targets for detection. Using the current planar technology, hundreds of the bulky sensors would be necessary for projects of this nature.

On the other hand, the capability exists to randomly disperse the MSPR sensors utilized in the present invention. However, until the present invention, there has been no way to capitalize on this ability to populate a sensor substrate with millions of SPR elements, each capable of being functionalized individually or in groups of spots. In accordance with the present invention, one method of achieving this discrete functionalization is to operate on groups of MSPR sensors by flowing droplets with reagents over specific spots 88 in FIG. 13 of the MSPR sensor chip using micro-fluidics. In other words, as seen in FIG. 13 the chip 72 may be divided into multiple spots, such as pointed out by 88. A micro-fluidics system may then flow a specific reagent droplets encapsulated by non-miscible carrier liquid like a perfluorinated oil that will not dissolve or mix with any aqueous solution over each MSPR domain 88 to commonly functionalize each MSPR sensor within the domain. Each spot may pertain to a different target analyte.

In another embodiment, the MSPR chip may be divided into bands and each band could be differently functionalized so that a like number of targets may be earmarked for detection.

In another approach, individual MSPR sensors may be precisely selected for specific functionalization. One manner of achieving this individual functionalization may be by use of a photo-activation bound cross-linker, such as photo-biotin. However, this method is inherently slow since only a few SPR sensors may be functionalized at a time. Another more versatile approach is to use a micro-spotter for making micro-arrays of MSPR sensors, in a manner similar to prior ink jet printers. Some micro-spotter printers are capable of placing ink drops to a resolution of 600×600 dpi, with dot sizes in the range of 30 μm at 45 μm spacing and a volume of only 10 pl.

Even more accurate ink jet printers are capable of resolutions of 4800×4800 dpi with each ink dot having a diameter of only 5 µm. This printing technique may be adapted to functionalize selected MSPR sensors or groups of sensors, resulting in functionalized spots, such as the spots 88 shown in FIG. 13. Each spot may pertain to a different target.

In yet another approach, discrete multiple target functionalization may be achieved using a multi-pin spotter. This multi-pin spotter may precisely apply the cross-linker or reagent directly to and only on the MSPR sensors. The specifically functionalized MSPR sensors may be in clusters or randomly dispersed throughout the entire field of MSPR sensors.

Figure 14:
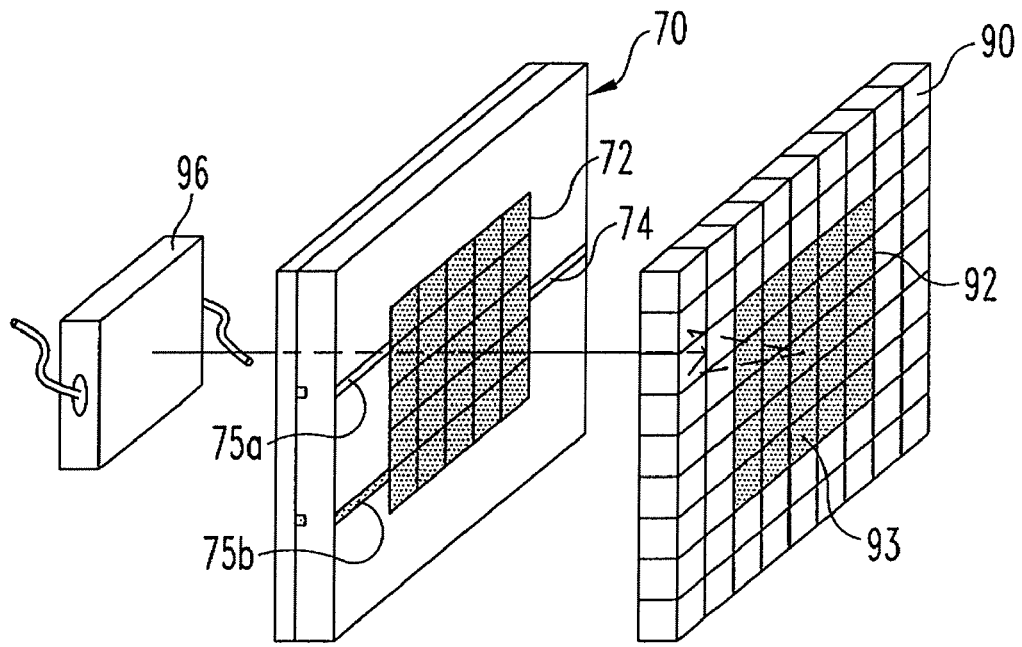
FIG. 14 is a direct-contact diagram of the components of a micro-fluidics sub-micron surface plasmon resonance sensor system in accordance with the present invention.

In a further approach to functionalization that is well suited to massively parallel processing, the MSPR sensors may be functionalized using a mask. The mask limits the application of the cross-linker or reagent to the MSPR sensors disposed within spots 88 on the substrate. It is contemplated that the functionalized spots will encompass random numbers of the randomly dispersed MSPR sensors on the array over an area that is significantly larger than the sensors themselves. Thus, in a specific embodiment, the functionalized spots may occupy an area about 30 µm in diameter, whereas the MSPR sensor have a diameter of about 1 µm. A micro-spotter capable of dispensing reagents in quantities as low as 10 µl may be used to functionalize the MSPR sensors in each spot. The sensor chip may include a bar code 86 or some other readable signature identifying the various functionalizations as well as spots corresponding to each functionalization. As described below, the bar code 86 may also contain calibration information corresponding to the responsive signals generated by the detector 90 (FIG. 14).

With the MSPR sensor construction as thus far described, a plurality of randomly dispersed MSPR sensors populates the substrate, with collections of sensors commonly functionalized to form spots 88. In the specific example shown in FIG. 13, twenty such spots are depicted; however, it is contemplated that hundreds, thousands and even millions of such spots may be defined on a given MSPR sensor chip. An operational MSPR sensor chip requires a light source and some form of detector to sense and record the resonant response at each spot. Thus, in accordance with one embodiment of the invention, a stack forming the micro-sensor may appear as shown in FIG. 14 with the MSPR sensor chip 72 sandwiched between the detector 90, which may be a CCD array, and the light source 96, which may be an LED. It is understood that various optical conditioning elements may be integrated with the light source and/or detector, such as an optical filter, to improve signal/noise ratio. The optical conditioning element may also include a wavelength filter or different discrete wavelength filters corresponding to specific spots 88 or individual MSPR sensors.

In accordance with one feature, the detector or CCD array may be mapped into a grid 92, with each pixel 93 of grid containing a CCD capable of sensing light transmission through the MSPR sensor chip 72 and configured to generate a signal indicative of that light transmission for subsequent processing. This mapped grid 92 overlays the MSPR sensor chip, as shown in FIG. 14, or alternatively the spots 88 may be regarded as projected onto the mapped grid, as illustrated in FIG. 13. Optimally, the detector grid is fine enough so that each spot 88 may be projected onto multiple pixels 93 of the grid. It is expected that each pixel may overlay several MSPR sensors, although the number of MSPR sensors corresponding to each pixel will vary due to the random distribution of the sensors on the substrate.

Calibration of the detector proceeds first by identifying an optimum pixel or pixels reading transmission data from each spot 88. Thus, in a specific example, a particular spot may fully encompass four pixels 93 and partially encompass five additional pixels. The MSPR chip is illuminated by the light source 96 and the measured intensity at each of the pixels corresponding to the spot is evaluated. The pixel registering the greatest response is selected as the pixel corresponding to the specific spot, which in turn corresponds to a specific functionalization. That selected pixel could likely map onto the largest number of MSPR sensors relative to the other pixels, hence its greater response relative to the other pixels. The output from the CCD within this selected pixel may then be calibrated in relation to the intensity and/or wavelength of the light source 96. The same process is repeated for all of the other functionalized spots 88. Thus, in the specific example, for the twenty functionalized spots (FIG. 13), eleven pixels 93 on the mapped grid of thirty six pixels 92 of the detector 90 may be identified so that the calibrated output of each pixel will be evaluated. This calibrated output may be written onto an on-board memory or transmitted to a peripheral memory device and/or processor. A calibration table with the calibration data for each of the mapped pixels may be maintained in a memory and accessed by the peripheral processor. The bar code 86, which could also be a magnetic strip, may thus provide an identifier for extracting the proper calibration table from multiple tables stored in memory. The calibration table may identify which pixels to read from the detector and how to interpret the output signal from each pixel. The peripheral device applying the calibration data may be configured to obtain the necessary data from a global database, such as through an Internet link.

It is contemplated that additional pixels may also be associated with a particular spot, with appropriate modifications to the calibration of the corresponding output responses. It should be appreciated that in some cases the output response for a given pixel may result from light transmission through only one MSPR sensor present within a given spot and aligned with a given pixel, while for another pixel the light transmission may be measured through several MSPR sensors. The random distribution of MSPR sensors means that the number of MSPR sensors used to generate an output signal corresponding to each functionalized spot is also random. However, the calibration step described above can ensure that the targets can be quickly and accurately detected. The high sensitivity of each MSPR sensor of the present invention means that even a single MSPR sensor may be sufficient for a particular functionalized spot and detector array pixel.

It can be appreciated that the device illustrated in FIG. 14 may open realms of target detection unavailable with prior sensor devices. As explained above, a single MSPR sensor chip may be functionalized to millions of targets in a small package (for example in the range of a few 1 $cm^2$). The small size of the sensors of the present invention allows the formation of massively parallel arrays of sensors or biosensors for DNA, RNA, toxins, pathogens, explosives, and protein detection. The use of micro-fluidics with the sensor chip allows for a continuous flow of test fluid across the sensor chip 70. This micro-fluidics feature facilitates the massively parallel sensor arrays and provides an avenue for real-time accurate sensing of chemical and biochemical conditions.

A particularly beneficial usage is in real-time detection of targets in the blood stream. One important application of the multi-channel embodiments of the present invention is in the detection of sepsis. Sepsis is a major source of mortality in post-surgery recovery and in trauma victims. Treatment of sepsis is largely limited to antibiotics and palliative measures to support heart, lung and kidney function. According to data collected in 2001, sepsis syndrome affects an estimated 751,000 patients in the United States each year, of whom 383,000 (51.1%) received intensive care. Mortality has been estimated at 215,000 deaths nationwide, increasing with age from 10% in children to 38.4% in those 85 years and older. The cost per case averages about $22,000, which sums up to almost $17 billion annually. Early detection of sepsis and rapid intervention (within two to four hours of onset) greatly reduces mortality and debilitation in survivors. However, no current method exists to monitor patients for the onset of sepsis. In many cases the medication produced for sepsis treatment failed due to the lack of instrumentation capable to continuously monitor cytokines levels in patients' blood.

Sepsis syndrome is the body's systemic inflammatory response to infectious stimuli. Endotoxins—such as lipopolysaccharide (LPS) from Gram-negative bacteria, peptidoglycans and flagellan from Gram-negative and Gram-positive bacteria, lipotechoic acid from Gram-positive bacteria, mannan from fungi, and other antigens from infectious agents—stimulate macrophages and monocytes to release tumor necrosis factor alpha (TNF-α), followed by a cascade of cytokine release. During the first period of sepsis (especially the first eight hours), excessive inflammatory response can cause massive organ damage, especially to kidneys and heart, but also reaching the liver, lungs and brain, requiring artificial support of blood pressure and ventilation. This organ damage often causes debility or mortality months or years after the acute phase of sepsis.

The release of pro-inflammatory mediators was originally thought to be largely uncontrolled. However, subsequent investigations have demonstrated that TNF-α also stimulates leukocytes to release anti-inflammatory cytokines, including IL-10, IL-1 and transforming growth factor-beta (TGF-β), which inhibit the synthesis of pro-inflammatory cytokines and exert direct anti-inflammatory effects on monocytes, macrophages, and endothelial cells. This compensatory anti-inflammatory response syndrome (CARS) is intended to localize what would otherwise be an uncontrolled pro-inflammatory response to the infection throughout the body. Unfortunately, the anti-inflammatory response often surpasses the pro-inflammatory response in the later phases of sepsis, resulting in immunoparalysis—i.e., the inability to mount an effective immune response to additional infectious insults.

Figure 15:
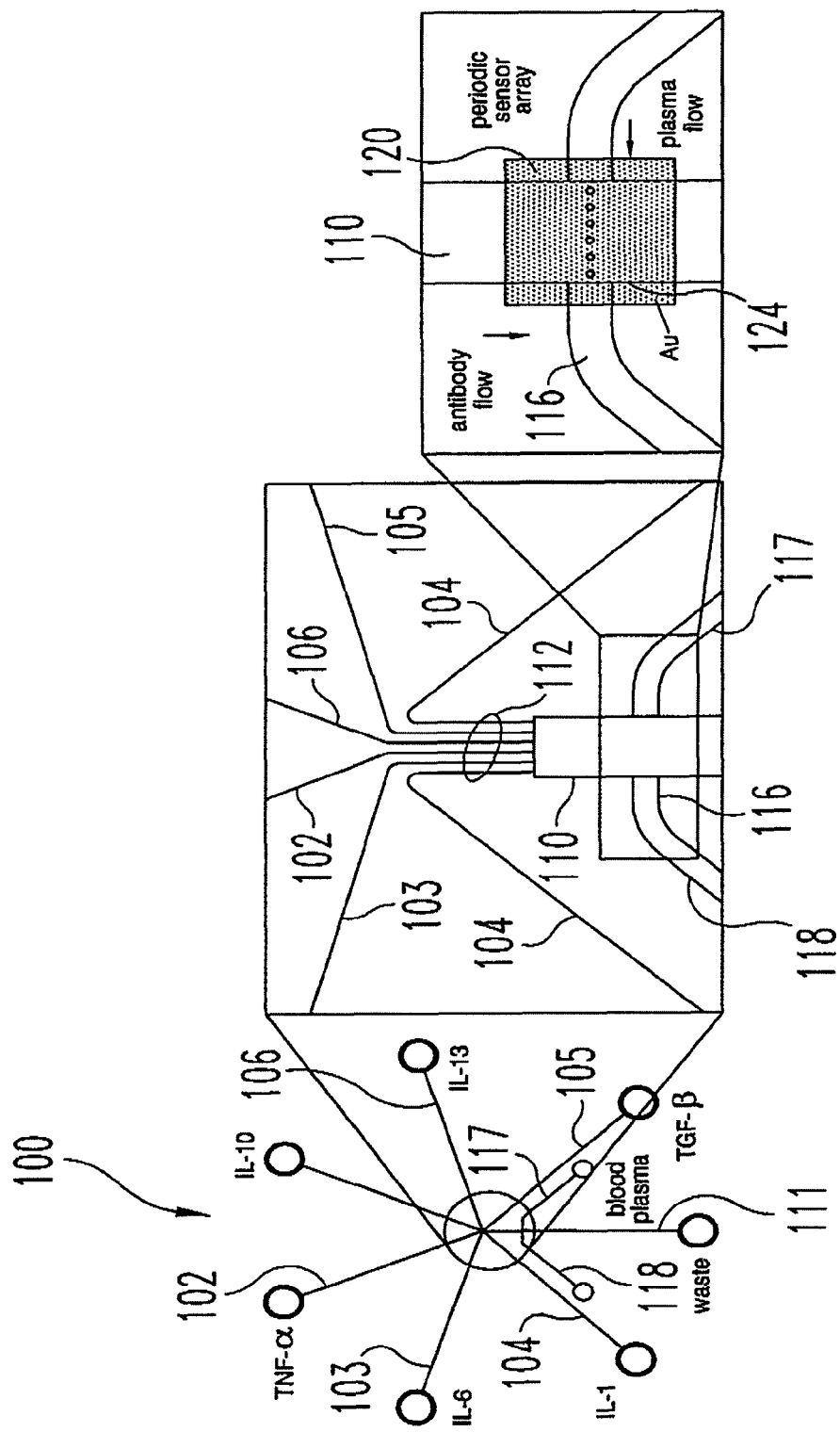
FIG. 15 is a schematic representation of an array of sub-micron surface plasmon resonance sensors according to the present invention that is capable of simultaneously evaluating multiple chemicals.

Thus, a minimally-invasive device, which could be attached to all postoperative and post-trauma patients which could monitor the onset and progress of sepsis in real time, allowing for much earlier and more directed intervention, and ultimately reducing both mortality and debility in survivors. In accordance with a particular embodiment, a micro-fluidics device 100, shown in FIG. 15, is provided that can be used to simultaneously analyze a set of six chemicals that play an important role in sepsis. (However, the micro-fluidic structure can be modified to accommodate the analysis of more or fewer chemicals at the same time, or may be modified for different driven flows, flow velocities or analysis set-ups). One manner of diagnosis of the onset of sepsis and its progress involves monitoring the chemicals, TNF-α, IL-1, IL-6, IL-10, IL-13 and TGF-β, at the same time and in real time. Thus, as shown in FIG. 15, the micro-fluidics sensor 100 includes a set of six channels 102-107 (each 50 μm wide, 100 μm apart and 11 mm long in a specific embodiment) that come together into a micro-fluidic chamber 110 (2 mm long and 600 μm wide), with each channel corresponding to a particular monitored chemical. The spacing is chosen so that diffusion of molecules of about 20 kDa will not interfere with molecules in the neighboring channels. These six channels are used to functionalize the sensor array 120 with specific antibodies for the above-mentioned chemicals. The flow of different antibodies through the micro-fluidic chamber will create a series of six parallel antibody stripes 112, functionalizing the chip. The chip 100 in this specific embodiment is designed for a flow of the antibody at a minimum 400 μm/s. This treatment and specific calibration can be done prior to usage of this chip to evaluate a sample.

A transverse channel 116 of 200 μm wide intersects the micro-fluidic chamber 110. This channel is wider to permit more viscous and faster coagulating fluids, like blood plasma, to pass though. The region of intersection covers an area of 200 μm×600 μm. The transverse channel 116 includes an inlet 117 through which the blood is introduced, and a waste outlet 118. Similarly, the micro-fluidic chamber 110 includes a waste outlet 111.

This sensor array 120 is preferably oriented at the intersection of the chamber 110 with the transverse channel 116 and preferably aligned with the channel. In one specific embodiment, the sensor 120 may include a linear array of six MSPR sensors 124 or sensor spots, with each individual sensor or sensor spot corresponding to a particular functionalization and aligned with the corresponding antibody strip 112.

The micro-fluidic device 100 depicted in FIG. 14 may be fabricated using a poly-dimethylsiloxane (PDMS) substrate and a cover glass in the manner set forth below. The devices are fabricated using negative-tone photoresist SU-8 as a master to cast PDMS channel structures. The master substrates are 50 mm×50 mm glass slides. The substrates are cleaned in $HCl:HNO_3$ (3:1), rinsed with nanopure water, dried with nitrogen, sonicated in methanol and acetone (1:1), and dried with nitrogen again. The master is created with two SU-8 photoresist layers. A first under-layer (an 18-20 μm thick layer of SU-8 2010) is used to promote adhesion of the channel structure to the substrate and a second thicker layer (60-80 μm in thick layer of SU-8 2070) of photoresist is used to create the channel structure. Bath layers are processed identically except that the first layer is exposed without a photomask. The photoresist is spin coated on the substrate at 1,000 rpm for 30 seconds and ramped at 40 rpm/second. After prebaking on a hot plate for one minute at 65° C. and two minutes at 95° C., the photoresist is then exposed to UV light. The proposed channel design is transferred to the photoresist through a photomask drawn using AutoCAD 2004 LT and printed on a transparency using a high resolution laser printer at 8,000 dpi. The UV exposure system is equipped with a high-pressure Hg arc lamp filtered to pass 360±23 nm, and the exposure dose is 300 $mJ/cm_2$. The exposed photoresist is post-baked on the same hot plate for one minute at 65° C. and three minutes at 95° C. The master is then developed for five minutes, rinsed with 2-propanol, and dried with nitrogen.

The silicone elastomer kit contains a polymer base and curing agent that are mixed in a 10:1 ratio for five minutes. A tape barrier is placed around the mold to hold the elastomer mixture, and the elastomer is poured onto the master. The PDMS on the mold is placed under low vacuum (~1 torr) for one hour to enhance channel replication and cured by heating at 120° C. for twenty minutes. The PDMS substrate is then separated from the master, and access holes for fluid connections to the channels are punched through the elastomer with a 16 G needle.

At the bottom of the PDMS mold, across the micro-fluidic chamber 110 at the intersection with transversal channel 116, the linear array of MSPR sensors 120 may be produced using photolithography and/or holographic optical tweezing, or any other suitable technique for placing microscopically small objects onto a glass substrate like using a micromanipulator and a laser tweezers system. The micromanipulator is loaded with a solution of $10^3$–$10^2$ nanopsheres/µL, precision-size-standard nanospheres. This concentration is chosen so that the MSPR sensor array 120 is dispensed having a spacing of about 50-100 µm. An optical laser tweezers can be used to hold the dielectric core (e.g., nanosphere, nanoparticle, nanobead) in place until the liquid dries and the next dielectric core (e.g. nanosphere, nanoparticle, nanobead) will be dispensed with the micromanipulator and held with the tweezers until the liquid dries and so on and so forth. Once the dielectric cores 124 are placed, the PDMS substrate is sputter coated through a window of 1 mm×1 mm placed above the intersection. The dielectric cores are covered with 150 nm of gold. The PDMS substrate and glass cover glass are then permanently joined after being exposed to air plasma for 40 seconds prior to contacting.

In one embodiment, a sepsis detector device may include a catheterization tube connected intravenously to the patient and to a pumping system to periodically draw a small volume of blood into the sensor device 100. The blood passes through a disposable filter to extract the plasma and the plasma is supplied to the disposable sensor 100 through a channel 116. The output from the sensor provides a reading of the cytokine concentrations in the plasma. The waste blood passes through channel 118 to be collected in a disposable biohazard-labeled discard tube. The small size of the MSPR sensor and sensor chip of the present invention allows the sensor device 100 and catheterization tube to be in place as long as the patient is under medical care. Control of the peristaltic micro-pump to draw blood into the sensor chip may be electronically controlled to occur at pre-determined intervals or in response to some other medical condition sensor. The detector of the sensor may be coupled to the same controller to generate an alarm if the particular agents are detected.

Elevated levels of IL-10, IL-13 and TGF-β indicate incipient sepsis, while elevated levels of IL-10, IL-13 and TGF-β indicate immunoparalysis. If the sensing time for each of the MSPR sensors is too large, a single channel may not be able to detect the cytokine levels in real time. In that case an array of channel detectors may be fabricated on a single disposable chip and the blood supply switched between channels at five minute intervals. A controllable microvalve may be used to alternately supply blood and clean sterile medium to the sensors to reset them for the next measurement.

Classes of agonist and antagonist drugs have been developed to control the various cytokines involved in sepsis. However, none of these drugs are widely used because physicians have no way to monitor their effects, which vary greatly from patient to patient and over time. The result is that the current treatment of choice includes inflammatory suppressors and enhancers that are given in either insufficient or excessive doses, both of which may be lethal to the patient. The MSPR sensors of the present invention would allow physicians to supply a tailored cocktail of agonists and antagonists which would suppress immune response early in infection and enhance it in late infection, while maintaining the cytokines at optimal levels at all times.

The same principles for detecting sepsis conditions may be applied to the interactive detection of other medical conditions, as well as an interface to collateral therapeutic devices. With appropriate functionalization, a single or multiple-sensor device may be used to monitor patient status during extended treatments. For instance, a MSPR sensor chip and micro-fluidics system in accordance with the embodiments described herein may be incorporated into a dialysis system, or other device that continuously draws blood or other bodily fluids from a patient for treatment. The MSPR sensor chip may be integrated into a continuous blood monitoring system to detect targets in real-time that are indicative of oncoming problems, such as heart attack, stroke, kidney failure and the like.

A second embodiment of the multiple sensor array devices may be provided that comprises of a set of syringe tubes containing cytokine regulatory drugs and controlled by the output of the cytokine detector prescribed above. This device would ultimately supply a controlled dosage of multiple cytokine regulators to the patent via an intravenous (IV) drip, continuously changing the supply of agonists and antagonists to keep the patient's cytokines at optimum levels. In the above blood monitoring example, the real-time detection of targets indicative of the onset of a heart attack, for instance, may be used to provide immediate real-time dosing in response to the onset of that condition.

This same interventional treatment may be employed to stave off sepsis when detected as described above. In this instance, certain anti-sepsis treatments rely upon the action of a particular protein to inhibit the creation of certain target molecules. However, the treatment itself may be immune-suppressant, so the treatment must be carefully administered. Real-time detection of target levels by the micro-fluidic MSPR sensor chip described herein allows prompt and accurate administration of the anti-sepsis treatment. A similar approach may be implemented to reduce the toxicity of chemo-therapy or HIV treatments, or for other treatments that create target blood-borne markers indicative of the onset or presence of unwanted side effects.

The disposable MSPR sensor devices described above are suitable for many other applications. For instance, the present invention may be adapted for public and private drinking water testing. The MSPR sensors may be functionalized to detect various organic and inorganic contaminants, toxins, cellular organisms and viruses. The sensors may be positioned within the water supply to continuously monitor the water flow for the selected targets. Since the devices of the present invention rely upon light detection devices, such as the CCD array 90 described above, an electrical signal is generated that may be evaluated and used to initiate a predetermined response, such as a sensible alert.

Devices based on these sensors can be developed for detection of biohazards, noxious chemicals, neurotoxins, explosives, or HIV or other viruses or bacteria in blood, plasma or other body fluids. The present invention allows the sensors to be small enough to be portable and easily disposable. In the illustrated embodiments, the sensor chip fits within a 50 mm×50 mm area. Specific apparatus can be adapted for airport or homeland security use or for use in water treatment plants or factories. Depending on the use, automated systems for connecting to the input reservoirs of the chip can be included and additional chemicals can be analyzed at the same time and on the same chip.

The MSPR sensors and micro-fluidics of the present invention may also be adapted to monitor chemical reactions or bioreactions. The micro-chips of the present invention may be integrated into fluid flow lines or directly within chemical reactors or bioreactors to detect certain target products of the reactions or to detect the chemical conditions within the reactors that may impact the reaction. The MSPR sensors may be used to optimize the reaction conditions or determine when the reaction is complete. This specific embodiment may have beneficial application as part of process control for drug or chemical fabrication, especially to control the purity of the resultant product.

Micro-fluidics devices endowed with the sub-micron cavity surface-plasmon biosensors of the present invention overcome several deficiencies in prior sensing techniques and devices. Combining the properties of the micro-fluidics devices with the sensitivity of the MSPR sensor extends the boundaries of the lab-on-a-chip ideal by increasing detection abilities inside the micro-fluidics chip or confined spaces.

Current devices monitor molecular interactions and molecular kinetics using planar SPR or the older ELIZA kits. In order to excite surface plasmons on a planar metal surface certain restrictions must be obeyed. In particular, the source of light must be p-polarized and a precise critical angle of incidence must be obtained in order to produce a maximum coupling between incoming photons and surface polaritons. The sensor of the present invention combines the sensitivity of surface plasmons with the resonant properties of a spherical sensor. Besides a boost in sensitivity, the invention relaxes constraints on the geometry and polarization of the light source. Moreover, the sensor has a footprint of a square micron or less, which makes it well-suited for miniaturization (having an active area of about one thousand times smaller than the present state-of-the-art SPR planar sensors) while increasing sensitivity and improving the ability to integrate into micro-fluidic structures. Furthermore, the MSPR sensors of the present invention work in transmission compared with the prior SPR sensors that work in reflection. Due to this difference, a sensing micro-fluidics chip incorporating the MSPR sensor of this invention can be placed very close between the light source and the sensing window of the detector, resulting in a very compact, robust and inexpensive hand-held device.

Micro-fluidics devices are currently the most sophisticated technology for dealing with small quantities of analyte (ranging from picoliters to microliters), and for very precise control of flows and gradients. They are appropriate for multiple replica molding and new configurations of channels and set ups can be produced at very low cost, making them suitable for single-use devices. This property makes them convenient in many areas of research, especially for medical applications. They are suitable for massively parallel processing of chemicals, which can save a huge amount of time, especially in analyzing very complex samples, for example, but not limited to, blood plasma, body fluids, toxic waste, foods, and the like. The only time constraint is the reaction time between the specific molecular species in the sample and the receptors bound to the surface of the functionalized MSPR detector.

The MSPR sensor of the present invention takes advantage of these properties of micro-fluidics devices. It has better sensitivity than prior devices due to the coupling of the surface-plasmon with the geometry of the sensor. While current SPR sensors can only detect large molecules, the SPR sensors of the present invention can detect large and small molecules with good sensitivity. The smallness of the sensors allows control, detection and analysis to be achieved on a single chip and to take advantage of the ability of micro-fluidics devices to conduct multiple parallel analyses, which can shorten the analysis time. Moreover, these devices can be disposable and can be produced cheaply.

In the illustrated embodiments, the microspheres are coated with gold. It is contemplated that the spheres may be coated with other metals, such as silver, copper, or other surface plasmon supporting metal. However, current experimentation suggests that spectral resonances in the transmitted light occur only for gold-coated dielectric submicron spheres, which is believed to be due to the surface plasmon coupling into stationary surface plasmon waves. The film thickness of the gold coating may be adjusted depending upon the application of the particular MSPR sensor. However, it has been found that increasing film thickness causes blue-shifting of the observed resonances, at least for the symmetric (low frequency) mode. Conversely, it has also been found that the frequency for the high frequency anti-symmetric mode is red-shifted with increases in film thickness. Moreover, the spherical geometry implemented in the present invention preferentially excites the symmetric surface plasmon modes, thereby minimizing red-shift effects. It has been observed that some peaks, such as the peak at 623 nm for a 770 nm dielectric core coated with a 150 nm gold layer, exhibits much less sensitivity to the metal film thickness than other peaks.

While the invention has been illustrated and described in detail in the drawings and foregoing description, the same should be considered as illustrative and not restrictive in character. It is understood that only illustrative, preferred embodiments have been presented and that all changes, modifications and further applications that come within the spirit of the invention are desired to be protected.

In the illustrated embodiments, the nano-particles forming the MSPR sensor are spherical in shape to form a resonant cavity. However, other symmetric geometric shapes may be utilized to form surface plasmon resonant cavities. For example, the sub-micron particle may have an elliptical shape or be multi-faceted like a dodecahedron, provided that the shape can sustain periodic boundary conditions for the stationary plasmon wave to travel across the surface of the particle.

The various materials and dimensions set forth for the illustrated examples may also be modified while still maintaining the functionality achieved by the MSPR sensor and micro-fluidics systems of the present invention. Modifications to the materials and dimensions of the MSPR sensor must still fulfill the primary object of the MSPR sensors of the present invention, namely to detect targets. Moreover, the modifications must not interfere with the shape or geometric resonant characteristics that are used to enhance the resonance quality of the micro-cavity sensor. The detection capability of the MSPR sensors of the invention relies upon binding the target to a coupling reagent layer that it itself bound to the surface plasmon-supporting coating, and ultimately upon the changes in optical response of the MSPR sensor emitted signal.

It is believed that for most targets and coupling reagents the wavelength of the applied light is not critical. On the other hand, the surface plasmon-supporting layer is, by definition, wavelength dependent since the surface plasmon coupling occurs in that layer. Thus, it is believed that modifications to the materials and dimensions of the MSPR sensor are centered on the selection of the surface plasmon-supporting layer material and its characteristic wavelength. In the illustrated embodiments, that material is gold which has a transmission peak at the wavelength of 510 nm. In accordance with certain aspect of the invention, this wavelength determines the diameter of the sub-micron particles 10 and the sub-wavelength pinhole 16. The sub-micron particle diameter is also a function of the refractive index of the dielectric material.

In alternative configurations, the surface plasmon-supporting coating material may be silver, copper, or other non-gold surface plasmon-supporting material, with appropriate changes in coating thickness. Since silver and copper each have a different characteristic surface plasmon wave, the selection of either metal as the material for coating 14 will result in a change in diameter for the sub-micron particle 10 and the sub-wavelength pinhole 16. In accordance with certain embodiments of the invention, the nano-particle diameter would be sized to about the characteristic wavelength of the surface plasmon wave excited in silver or copper films, while the pinhole diameter would be fixed at less than that wavelength. Similarly, the coating thickness may be modified with a commensurate change in the micro-particle and sub-wavelength pinhole diameters.

To the extent that the MSPR sensor dictates the characteristic wavelength, the light source and transmitted light detector (such as the source 96 and detector 90 in FIG. 14) may be selected accordingly. In certain embodiments, white light may be acceptable, while in other embodiments it may be desirable to select a monochromatic light source centered at the characteristic wavelength of the MSPR sensor. Preferably the light detector is calibrated to the characteristic resonant wavelength.

With respect to material selection for the MSPR sensors and micro-fluidics chips of the present invention, the materials in the above examples and embodiments are illustrative. While the MSPR sensors are described as formed of polystyrene nanospheres, other light transmissive materials may be used, such as glass, silica, aluminum oxide, alumina, titania, zirconia, zirconium sulfate, PMMA, melamine, polylactide, radioactive oxides, or magnetic compounds. The selected material is most preferably dielectric and has an index of refraction larger than of the reagent medium. As indicated above, the index of refraction of the sub-micron dielectric core material affects the optical response and resonant mode of the MSPR sensor, as does with the surface plasmon-supporting coating.

Likewise, the material forming the housing or chip around the MSPR sensors and the substrate may be different from the PDMS material identified in the illustrated examples and embodiments. Preferably, the material is substantially light transparent and exerts only a minimal influence on the optical and resonance characteristics of the MSPR sensor.

With respect to applications or uses of the micro-fluidic MSPR sensors chips and devices of the present invention, the foregoing examples and embodiments are not intended to be limiting. It should be appreciated that the present invention permits the rapid and accurate detection of a wide range of targets, whether in small sample volumes or in continuous flow systems. The present invention also permits simultaneous detection of hundred, thousands and even millions of targets in a single MSPR sensor chip or in a massively parallel array of MSPR sensors.

What is claimed is:

1. A wearable device for monitoring the concentration of one or more target analytes, ligands, or molecules in a body fluid comprising:
   a conduit adapted to connect to the patient's bodily fluid; and;
   a sensor chip, wherein the sensor chip comprises
   a light transmissive substrate;
   a housing formed of a light transmissive material and defining at least one fluid cavity in communication with at least one fluid inlet for receiving the body fluid and at least one fluid outlet;
   one or more micro-cavity surface plasmon resonance (MSPR) sensors mounted on a surface of the light transmissive substrate;
   a light source arranged to direct light toward the MSPR sensors; and
   a detector arranged relative to the one or more MSPR sensors to detect their emitted light;
   wherein the one or more MSPR sensors are mounted randomly or non-randomly over a spatial domain of said surface;
   an exposed surface of each MSPR sensor is functionalized with a surface treatment, or a surface coating of a material capable of binding with the one or more targets to be detected;
   each MSPR sensor includes a light transmissive core formed in a geometric shape that can sustain periodic boundary conditions for a stationary surface plasmon waves to travel across the outer surface thereof; and a pinhole is defined at the interface between each MSPR sensor and the substrate; and
   the conduit is in communication with at least one of the fluid inlets.

2. The wearable device of claim 1 wherein the light source is at least one light-emitting device.

3. The wearable device of claim 1 wherein the light detector includes an array of pixels, each pixel operable to generate an output in response to the detection of light at said pixel.

4. The wearable device of claim 3 wherein there is a plurality of MSPR sensors where the plurality of MSPR sensors are randomly or non-randomly distributed over the array of pixels.

5. The wearable device of claim 4 wherein there is a plurality of targets.

6. The wearable device of claim 5 wherein the plurality of MSPR sensors are in a plurality of groups where each MSPR sensor in a group is commonly functionalized with a surface treatment, or a surface coating of a material capable of binding with one of the targets.

7. The wearable device of claim 6, wherein the groups of commonly functionalized MSPR sensors are arranged in a plurality of columns wherein in each column contains one of the groups of commonly functionalized MSPR sensors; and said housing defines a flow channel over each of said plurality of columns.

8. The wearable device of claim 4 wherein the body fluid is blood.

9. The wearable device of claim 8 wherein the targets are biomarkers for a disease or condition.

10. The wearable device of claim 9 wherein the targets are selected from the group consisting of blood markers for sepsis, cytokines, growth factors, and tumor markers.

11. The wearable device of claim 10 wherein the targets are interleukin-1, interleukin-6, interleukin-10, interleukin-13, transforming growth factor-$\beta$, and tumor necrosis factor-$\alpha$ or any other biomarkers.

12. The wearable device of claim 1, further comprising a micro-fluidic channel.

13. The wearable device of claim 1, further comprising a micro-fluidic pump.

14. The wearable device of claim 1, wherein said fluid inlet includes at least a micro-fluidic valve.

15. The wearable device of claim 1, wherein said housing further defines at least one additional fluid inlet in communication with said cavity.

16. The wearable device of claim 15, wherein said additional fluid inlet includes at least a micro-fluidic valve.

17. The wearable device of claim 1, wherein at least one of said fluid inlets includes a filter for controlling fluid quality in said cavity.

18. The wearable device of claim 1 further comprising a strap, an adhesive pad, or a combination thereof.

19. The wearable device of claim 1 further comprising a system of communication with a remote station.

20. An implantable device for monitoring the concentration of one or more target analytes, ligands, or molecules in a body fluid comprising:

a conduit adapted to connect to the patient's bodily fluid; and;

a sensor chip, wherein the sensor chip comprises a light transmissive substrate;

a housing formed of a light transmissive material and defining at least one fluid cavity in communication with at least one fluid inlet for receiving the body fluid and at least one fluid outlet;

one or more micro-cavity surface plasmon resonant (MSPR) sensors mounted on a surface of the light transmissive substrate;

a light source arranged to direct light toward the MSPR sensors; and a detector arranged relative to the one or more MSPR sensors to detect emitted light;

wherein the one or more MSPR sensors are mounted randomly or non-randomly over a spatial domain of said surface;

an exposed surface of each MSPR sensor is functionalized with a surface treatment, or a surface coating of a material capable of binding with the one or more targets to be detected;

each MSPR sensor includes a light transmissive core formed in a geometric shape that can sustain periodic boundary conditions for a stationary surface plasmon waves to travel across the outer surface thereof; and a pinhole is defined at the interface between each MSPR sensor and the substrate; and the conduit is in communication with at least one of the fluid inlets.

21. The implantable device of claim 20 wherein the light source is at least one light-emitting device.

22. The implantable device of claim 20 wherein the light detector includes an array of pixels, each pixel operable to generate an output in response to the detection of light at said pixel.

23. The implantable device of claim 22 wherein there is a plurality of MSPR sensors where the plurality of MSPR sensors are randomly or non-randomly distributed over the array of pixels.

24. The implantable device of claim 23 wherein there is a plurality of targets.

25. The implantable device of claim 24 wherein the plurality of MSPR sensors are in a plurality of groups where each MSPR sensor in a group is commonly functionalized with a surface treatment, or a surface coating of a material capable of binding with one of the targets.

26. The implantable device of claim 25, wherein the groups of commonly functionalized MSPR sensors are arranged in a plurality of columns wherein in each column contains one of the groups of commonly functionalized MSPR sensors; and said housing defines a flow channel over each of said plurality of columns.

27. The implantable device of claim 23 wherein the body fluid is blood.

28. The implantable device of claim 27 wherein the targets are biomarkers for a disease or condition.

29. The implantable device of claim 27 wherein the targets are selected from the group consisting of blood markers for sepsis, cytokines, growth factors, and tumor markers.

30. The implantable device of claim 27 wherein the targets are interleukin-1, interleukin-6, interleukin-10, interleukin-13, transforming growth factor-β, and tumor necrosis factor-α.

31. The implantable device of claim 20 further comprising at least a micro-fluidic channel.

32. The implantable device of claim 20, further comprising a micro-fluidic pump.

33. The implantable device of claim 20, wherein said fluid inlet includes at least a micro-fluidic valve.

34. The implantable device of claim 20, wherein said housing further defines at least one additional fluid inlet in communication with said cavity.

35. The implantable device of claim 34, wherein said additional fluid inlet includes at least a micro-fluidic valve.

36. The implantable device of claim 20, wherein at least one of said fluid inlets includes a filter for controlling fluid quality in said cavity.

37. The implantable device of claim 20 wherein the implantable device is encapsulated in a biocompatible material.

38. The implantable device of claim 20 further comprising a system to attach the device to an organ, a specific tissue or any desired location inside the body.

39. The implantable device of claim 20 further comprising a system of communication with a remote station.

* * * * *